United States Patent
Siegel et al.

(10) Patent No.: US 9,779,216 B2
(45) Date of Patent: *Oct. 3, 2017

(54) SYSTEMS AND METHODS FOR STORING AND DISPENSING MEDICATION

(75) Inventors: Todd Siegel, Clearwater, FL (US); Ron Rosenbaum, Clearwater, FL (US)

(73) Assignee: MTS Medication Technologies, Inc., Clearwater, FL (US)

( * ) Notice: Subject to any disclaimer, the term of this patent is extended or adjusted under 35 U.S.C. 154(b) by 97 days.

This patent is subject to a terminal disclaimer.

(21) Appl. No.: 12/399,519

(22) Filed: Mar. 6, 2009

(65) Prior Publication Data

US 2010/0004782 A1    Jan. 7, 2010

Related U.S. Application Data

(63) Continuation of application No. 10/846,243, filed on May 14, 2004, now Pat. No. 7,502,666.

(51) Int. Cl.
*G06F 17/00* (2006.01)
*G06F 19/00* (2011.01)
*A61J 1/03* (2006.01)

(52) U.S. Cl.
CPC ............ *G06F 19/3462* (2013.01); *A61J 1/03* (2013.01); *A61J 1/035* (2013.01)

(58) Field of Classification Search
CPC .......... G06F 19/3462; A61J 1/03; A61J 1/035
USPC ........................ 700/236, 237, 241, 242, 244
See application file for complete search history.

(56) References Cited

U.S. PATENT DOCUMENTS

| | | | |
|---|---|---|---|
| 4,526,474 A | 7/1985 | Simon | |
| 4,616,316 A | 10/1986 | Hanpeter et al. | |
| 4,660,991 A | 4/1987 | Simon | |
| 5,412,372 A | 5/1995 | Parkhurst et al. | |
| 5,836,474 A | 11/1998 | Wessberg | |
| 5,883,806 A | 3/1999 | Meador et al. | |
| 6,011,999 A | 1/2000 | Holmes | |
| 6,175,779 B1 | 1/2001 | Barrett | |
| 6,219,587 B1 * | 4/2001 | Ahlin et al. | 700/233 |
| 6,335,907 B1 | 1/2002 | Momich et al. | |
| 6,539,281 B2 | 3/2003 | Wan et al. | |
| 6,636,780 B1 * | 10/2003 | Haitin et al. | 700/236 |

(Continued)

FOREIGN PATENT DOCUMENTS

WO    02-38101    5/2002

OTHER PUBLICATIONS

International Patent Application No. PCT/US05/16978, International Search Report and Written Opinion, dated Jun. 30, 2008, 3 pages.

(Continued)

*Primary Examiner* — Michael K Collins
(74) *Attorney, Agent, or Firm* — Kilpatrick Townsend & Stockton LLP

(57) ABSTRACT

A medication storage/dispenser unit comprises a processor connected to medication package storage compartments. The storage compartments comprise a medication package, and preferably may also include a content reader, a medication information reader, and a medication package indicator. The processor receives a medication request from the medical information system, receives content and other medication from the storage compartments, processes the information and automatically opens the appropriate compartment with the correct medication.

13 Claims, 24 Drawing Sheets

(56) References Cited

U.S. PATENT DOCUMENTS

| | | | |
|---|---|---|---|
| 6,771,174 B2 | 8/2004 | Broas | |
| 7,052,097 B2* | 5/2006 | Meek, Jr. | E05B 47/0002 312/209 |
| 7,142,944 B2* | 11/2006 | Holmes | A47B 88/00 221/4 |
| 7,155,306 B2* | 12/2006 | Haitin et al. | 700/242 |
| 7,264,136 B2* | 9/2007 | Willoughby et al. | 221/3 |
| 7,502,666 B2* | 3/2009 | Siegel et al. | 700/244 |
| 8,019,471 B2* | 9/2011 | Bogash et al. | 700/242 |
| 8,554,364 B2* | 10/2013 | Holmes | A47B 88/00 700/232 |
| 2003/0105554 A1 | 6/2003 | Eggenberger | |
| 2003/0120384 A1* | 6/2003 | Haitin et al. | 700/242 |
| 2004/0104652 A1* | 6/2004 | Holmes | A47B 88/00 312/348.3 |
| 2004/0108795 A1* | 6/2004 | Meek, Jr. | E05B 47/0002 312/218 |
| 2004/0178112 A1 | 9/2004 | Snyder | |
| 2010/0089789 A1* | 4/2010 | Rosenbaum et al. | 206/531 |
| 2010/0089791 A1* | 4/2010 | Rosenbaum et al. | 206/531 |

OTHER PUBLICATIONS

International Patent Application No. PCT/US05/16978, International Preliminary Report on Patentability, dated Mar. 3, 2009, 4 pages.

U.S. Appl. No. 10/846,243, Non-Final Office Action dated Dec. 6, 2006, 7 pages.

U.S. Appl. No. 10/846,243, Final Office Action dated Jul. 10, 2007, 6 pages.

U.S. Appl. No. 10/846,243, Non-Final Office Action dated Feb. 7, 2008, 7 pages.

U.S. Appl. No. 10/846,243, Notice of Allowance dated Oct. 20, 2008, 6 pages.

* cited by examiner

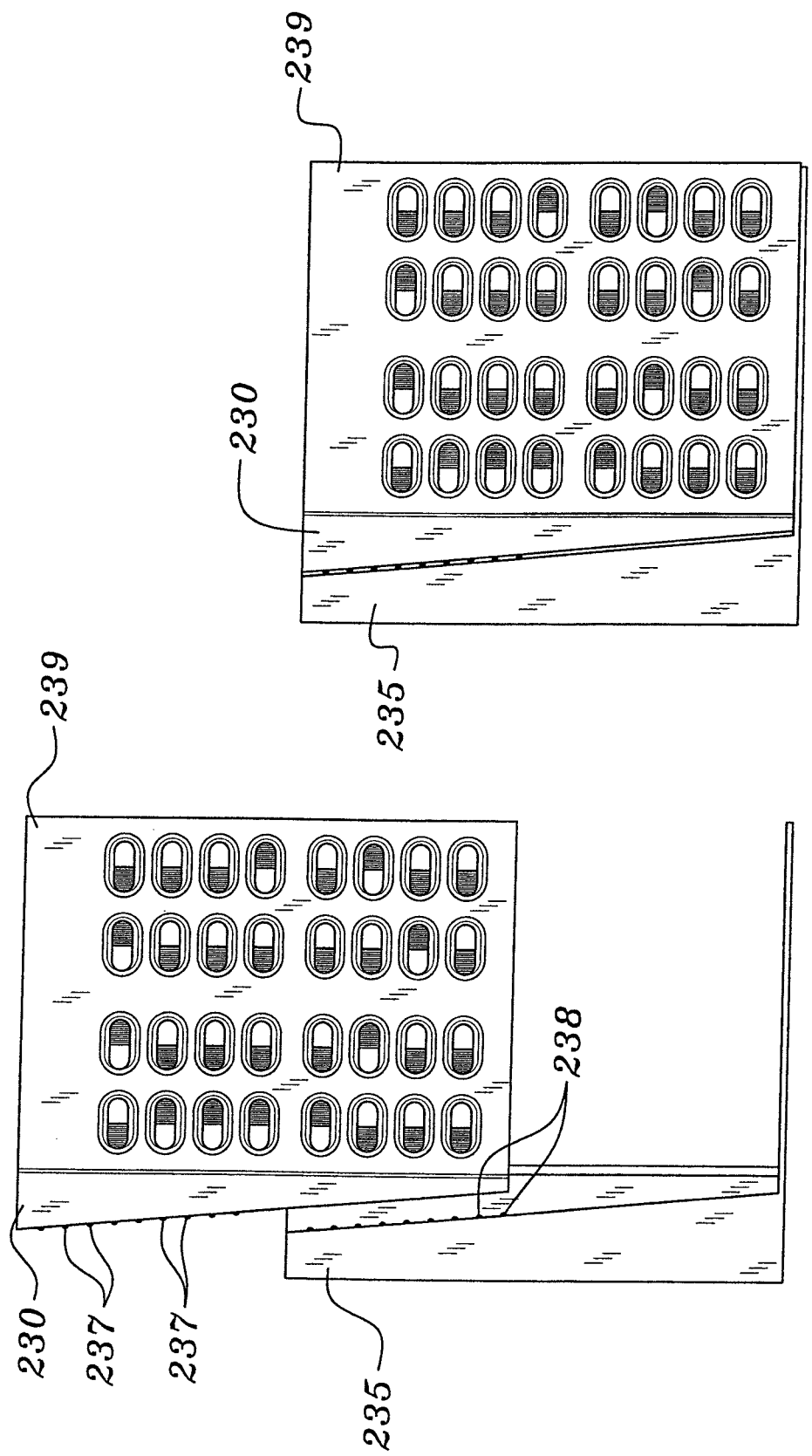

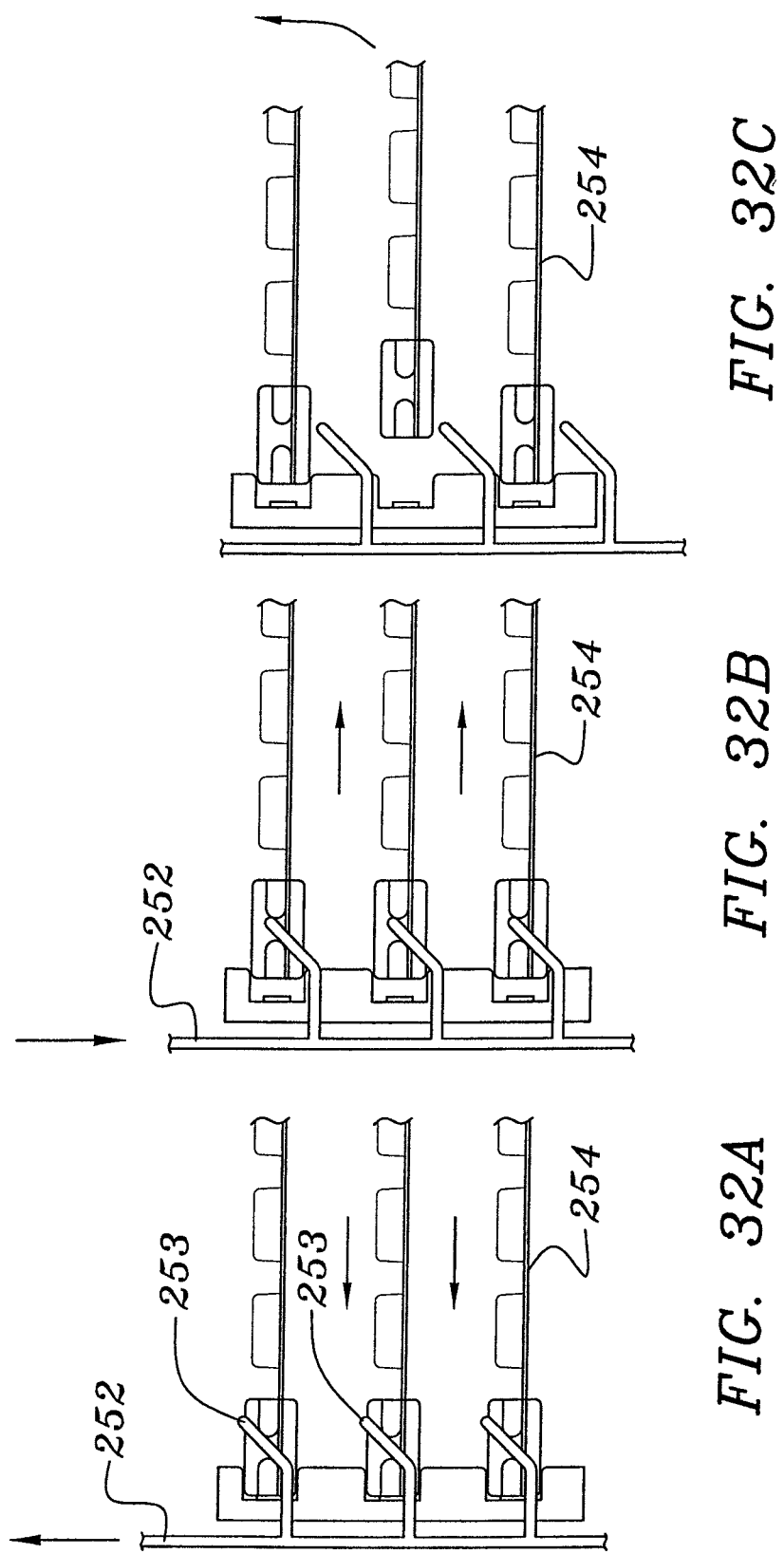

SYSTEMS AND METHODS FOR STORING AND DISPENSING MEDICATION

The subject matter of application Ser. No. 10/846,243 is incorporated herein by reference. The present application is a continuation of U.S. application Ser. No. 10/846,243, filed May 14, 2004, now U.S. Pat. No. 7,502,666, issued Mar. 10, 2009, the entire contents of which is incorporated herein by reference.

BACKGROUND OF THE INVENTION

1. Field of the Invention

The present invention relates, in general, to the field of medication dispenser systems. More specifically, the present invention is directed to a variety of systems and methods which may be used for storage and dispensing medication.

2. Description of the Related Art

The present invention overcomes the shortcomings and the deficiencies of the prior art and is directed to systems and methods which solve or at least substantially reduce the impact of problems associated with existing pharmaceutical and medication dispenser systems.

Currently in the field of medication dispensing systems, a typical system includes a computer controlled machine which stores, processes, and packages medication for distribution. The computer receives a patient's prescription, processes the appropriate dosage, and dispenses the unpackaged medication into containers or packages. The packages may work in a number of different settings for a specific patient or the package may contain a single specific product. Such conventional solid pharmaceutical packaging systems provide many advantages in large pharmacy formularies and pharmaceutical distribution centers primarily due to the physical size of the packaging device.

Personal medication with individual packages that group medications based on their administration times as well as several packages of individual medications divided by dosage are well known in the art. Such existing systems provide advantages for distribution, but many problems remain.

One significant deficiency of conventional automated dispensing systems is that they require considerable resources. For example, existing systems require sophisticated management software to process, retrieve, dispense, and track the different medications. In addition, they are often very large and require dedicated space. Finally, such systems are also very expensive and are unavailable or impractical for smaller healthcare facilities, such as nursing homes, local pharmacies, and individual hospital floors.

Many health care facilities still use distribution pharmacies in which employees inventory, process and distribute the medication. This is undesirable because several studies have shown that human error is a significant cause in the distribution and administration of incorrect medication. Administration of incorrect medication can result in mistreatment, severe health complications and even death. However, studies have also shown that such problems are significantly reduced when automated dispensing systems are utilized. Automated dispensing systems are typically used to store and provide access to the prescription medications based on a doctor's order.

Another deficiency of existing systems is that they are inefficient in situations where several medications need to be dispensed at schedules times and in situations where medications must be dispensed immediately such as in hospital emergency rooms or when a new patient is admitted to a nursing home and the medications for the individual have not yet been delivered. In existing systems, healthcare providers or other appropriate individuals request the medication from the operator of the automated dispensing system typically located at a different central location. The operator then processes the appropriate medication and arranges for its physical transportation to the requesting healthcare provider.

Large health care facilities use a system of transportation tubes or elevators to reduce the delivery times. Smaller facilities such as nursing homes and local pharmacies do not contain such elaborate transport systems. Accordingly, medications are manually transported to several locations.

By way of example, in nursing homes all the medication must be administered from a medication cart that is pushed up and down the hall. Often times, the medications are delayed in the transport result in the administration of the medicine at the wrong time. Unfortunately, administration of incorrect medication has become pervasive not only in nursing homes but also in healthcare facilities such as hospitals. This is especially disastrous in emergency situations where healthcare providers must immediately evaluate patients, quickly administer care to stabilize a patient's condition.

In nursing homes, fishing tackle boxes are currently used for distributing controlled substances directly to patients. Once a pharmaceutical product has been removed from the tackle box, the entire box must be returned to the pharmacy from which it was provided so that the pharmacy may properly account for the use of the pharmaceutical products contained within the fishing tackle box.

The present distribution of controlled substances in this matter has numerous shortcomings because there is too great a potential for the theft of the pharmaceutical products and inadequate inventory control of the products.

Personalized packaging that is prepared in a remote location solves some of the existing problems but many issues still remain. For example, there remain problems relating to access and control of the pharmaceutical products, even when they have been previously packaged. Even though packaging may be personalized, it is still possible for a health care worker to administer incorrect medications. Furthermore, there is the issue of controlling access to medications. This is a particularly important problem related to the handling of controlled substances. Additionally, in healthcare facilities where packaging of pharmaceuticals is personalized, a problem exists relating to the issue of unused medication.

The present invention overcomes the shortcomings and deficiencies of the prior art and is directed to systems and methods which solve or at least substantially reduce the impact of these problems associated with existing medication dispensing systems.

One object and advantage of the present invention is to provide a system which stores and dispenses medication from an individual storage/dispenser unit.

It is another object and advantage of the present invention to provide a system that comprises an independent medical information system.

It is further an additional object and advantage of the present invention to provide a system that may be used with any individual medical information unit within a medical information system.

It is further an object and advantage of the present invention to provide a system which is small in size.

It is yet another object and advantage for the present invention to provide a system which can be readily transported.

It is still further another object and advantage of the present invention to provide a system which may be used by individuals without specialized expertise.

It is yet another object and advantage of the present invention to provide a system which is cost effective for both small and large healthcare facilities as well as other medication dispensing facilities.

It is yet another additional object and advantage of the present invention to provide a system that is more secure than existing automated dispensing systems.

The above and other objects, advantages, and features of the present invention will become readily appreciated and understood from consideration of the following detailed description of the preferred exemplary embodiments of the present invention when taken together with the accompanying drawings of the present invention.

SUMMARY OF THE INVENTION

The present inventions are directed to a wide variety of systems and methods for storing, processing, and dispensing medication. The systems and methods of the present invention are extremely flexible and are easily capable of processing and dispensing various amounts of medications that are prescribed for a number of individuals.

In accordance with a first preferred exemplary embodiment of the present invention, the medication dispensing systems and methods employ a medical information system connected to a separate storage and dispenser unit which probably has its own processor. This separation and ability of each to operate independently provides added security because a compromise of one does not comprise the proper functionality of the other. The medical information system comprises one or a group of computers, servers, or any other devices which are capable of processing, storing, and retrieving various information. Those skilled in the art will appreciate that the prescription management system may be a stand alone device or a device connected to a network via the internet, intranet, virtual private network, or other communications protocol.

In the preferred exemplary embodiment, the medical information system comprises a computer with access to a patient's records and prescription information and is either directly or indirectly connected to the storage/dispenser unit. Those skilled in the art will appreciate that the medical information system can also be connected to the storage/dispenser via the internet, intranet, virtual private network, or other communications protocols, such as, wireless or infrared techniques. This is advantageous because the dispenser unit can be transported from one location to another without moving the medical information system. Moreover, the storage/dispenser unit may be remotely controlled to dispense medication from a separate location. For example, in situations where a pharmacist is needed for drug interaction consultation, the pharmacist can check the prescription and the patient's records at his/her location and dispense the medication from the storage/dispenser unit located at the patient's or health care provider's location.

In the preferred exemplary embodiment, the storage/dispenser unit comprises a processor and several storage compartments. The processor compares incoming information from the medical information system to the information provided by the storage compartments within the storage dispenser unit. When a desired medication is available, the processor automatically opens the appropriate storage compartment in a preferred exemplary embodiment.

In the preferred exemplary embodiment, the storage/dispenser unit also comprises storage compartments connected to the processor. Those skilled in the art will appreciate that the storage compartments may be connected to the processor via a direct wired connection such as, or example, a ribbon cable, SCSI, IDE, as well as other connection methods. In the preferred exemplary embodiment, the storage compartment also preferably comprises at least one mechanism for reading information from a blister package such as medication information, content of the blister package, dosage information, or other information that may be provided by the medication blister package. Those skilled in the art will appreciate that existing blister packages with means for providing information, such as bar codes or magnetic strips can be utilized with the preferred exemplary embodiment of the present invention. Similarly computer ships, RF ID tags and/or text reading mechanisms are suitable for use in reading the information from the packaging devices.

This significantly reduces tracking problems associated with systems where a particular medication is added to the automated dispensing system in bulk or where the information about the medication is input manually into the system. In the preferred exemplary embodiment, each storage compartment also comprises indicators which specifically identify the desired blister package.

In addition to the various systems and methods directed to the storage and distribution of solid pharmaceutical products while providing controlled access to the individual product packages, the systems and methods described herein also include a variety of innovative solid pharmaceutical product packaging solutions which are able to provide information concerning whether individual doses have been removed from individual product package cavities. Specific implementations include blister package members wherein electric circuits individually cross over the backing material on the blister package cavity so that when the solid pharmaceutical product is removed from the blister package, an electronic interface can instantaneously and automatically determine whether the dose has been removed. Advantageously, this allows the distribution system to determine how many individual doses of a particular product remain, and it is also useful in controlling access to the solid pharmaceutical products. Additionally, various bar code and other reading mechanisms are provided for determining both the content and location of the individual package members.

In alternate embodiments of the present invention, blister package card member storage frames are provided which are individually inserted into a drawer of the storage cart in accordance with a preferred alternate exemplary embodiment of the present invention. Advantageously, the storage cart includes individual slots for receiving the frames and/or solid pharmaceutical blister package card members. In accordance with a preferred exemplary embodiment the control system automatically lights an appropriate slot containing the appropriate solid pharmaceutical product package for a desired patient.

A variety of different types of frames for receiving the blister package members may be utilized in order to automatically provide information regarding location and usage of the individual solid pharmaceutical product package members. In addition to the use of the frames and/or solid pharmaceutical product blister package cards, there are also a variety of access control systems directed to limiting access to the individual solid pharmaceutical package cards. For example, in an alternate preferred exemplary embodiment of the present invention, a rotary distribution member is provided with one or more reading devices that are capable of reading both the type of solid pharmaceutical product package as well as the number of doses that have been removed from the individual solid pharmaceutical product package containing members.

In alternate embodiments of the present invention, a linear optical scanning mechanism is provided for identifying the number of doses that have been removed from a package when the blister package card is inserted and/or removed from the slot of the distribution system. Alternatively, electronic reading mechanisms may be provided with a variety of different access apparatus in order to ensure that the electronic reading of the card is accurately determined. For example, in an alternate embodiment, an angled reading arrangement is provided which relies upon gravity to ensure that adequate electrical contact has been made.

In a further alternate embodiment of the present invention, levers which provide mechanical cam action are used to secure a reading device onto electrical contacts of the individual pharmaceutical packages. In yet additional alternate embodiments access limiting devices are provided in order to physically secure the solid pharmaceutical product package members in the storage drawers of the distribution system.

BRIEF DESCRIPTION OF THE DRAWINGS

FIG. 29 illustrates an alternate preferred exemplary embodiment of the present invention;

FIG. 32 illustrates an alternate preferred exemplary embodiment of the present invention;

DETAILED DESCRIPTION OF THE INVENTION

While various embodiments of the present invention are discussed in detail below, it should be appreciated that the present invention provides inventive concepts that can be embodied in a wide variety of specific contexts. The specific embodiments discussed are merely illustrative of specific ways to make and use the invention and do not limit the scope of the invention.

Figure 1:
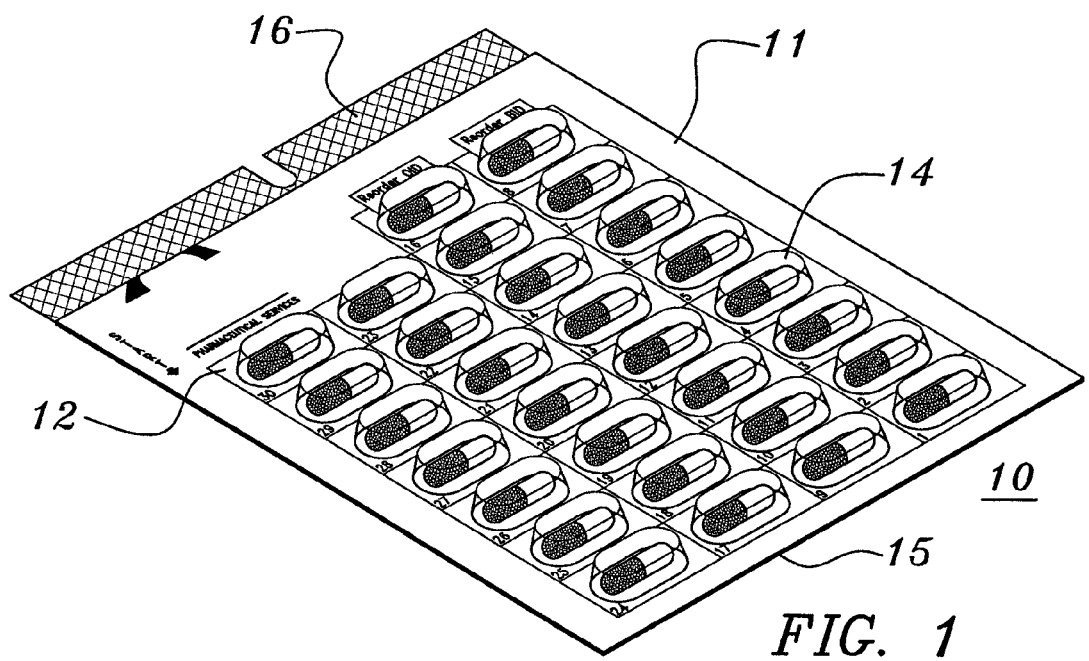
FIG. 1 shows a medication blister package utilized by the present invention.

FIG. 1, illustrates a first preferred exemplary embodiment of a medication blister package that is shown generally at 10, and which may be utilized by the pharmaceutical storage distribution and control system of the present invention. The overall blister package comprises a top board cover 11, preferably comprised of cardboard, a clear plastic sheet portion 12 with blister cavity protrusions 14 and a board backing 15 on the underside. The blister package 10 is used for storing individual medications/pills in the individual blister cavities. The top board cover 11 of the blister package 10 may also include writing or other description information such as the medication's name, or dosage, and/or patent information. In the preferred exemplary embodiment, the blister package 10 also comprises an electrical contact region 16. The electrical contact region 16 provides connection to electrical circuitry that is used to determine which medications/pills are still available in each package.

Figure 2:
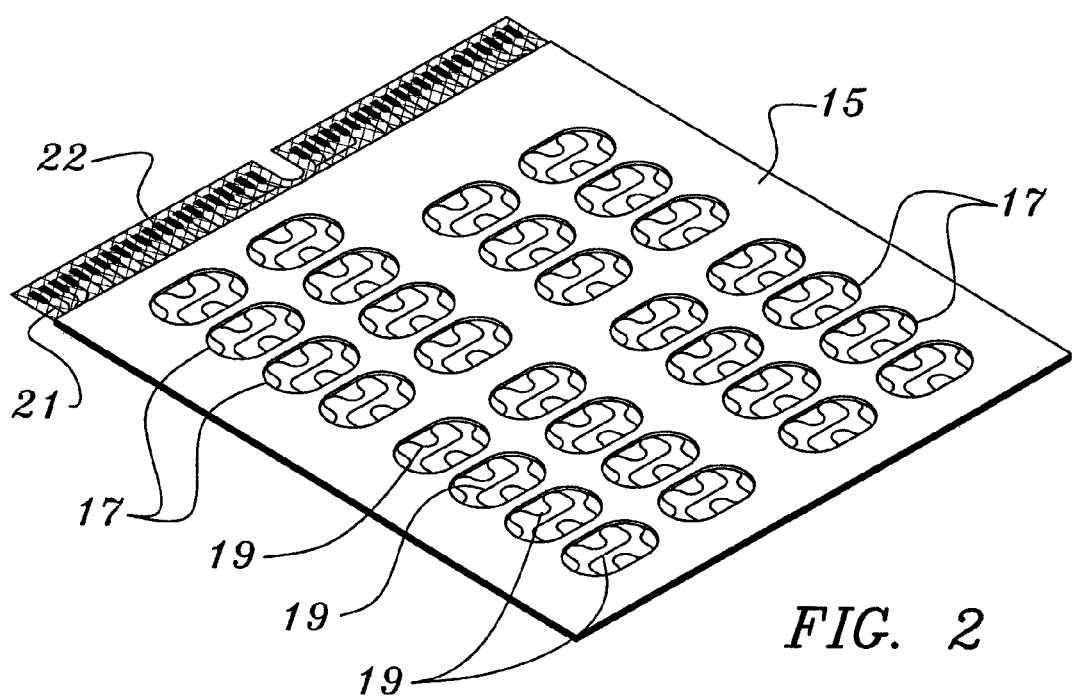
FIG. 2 displays a back side of the blister package.

FIG. 2 illustrates a back side of the blister package 10 that is shown in FIG. 1. The top board cover 11 and the backing 15, usually comprised of cardboard or any solid material, secure the clear plastic material sheet 12 therebetween. The backing 15 also comprises openings 17 associated with the blister protrusions or cavities 14 that can be easily broken for the purpose of retrieving one or more individual medications from the blister package 10. In an unused blister package 10, the openings 17 may be covered with an easily punctured material such as paper or foil to provide easy access to the medication within their associated blister protrusions. FIG. 2 also illustrates the individual electrical circuit switches or conductive members 19, which are broken or open circuited when a pill or dose is removed from a specific cavity. FIG. 2 also illustrate individual wiring members 21, that extend into the electrical contact region 16 and corresponding electrical contacts 22.

Figure 3:
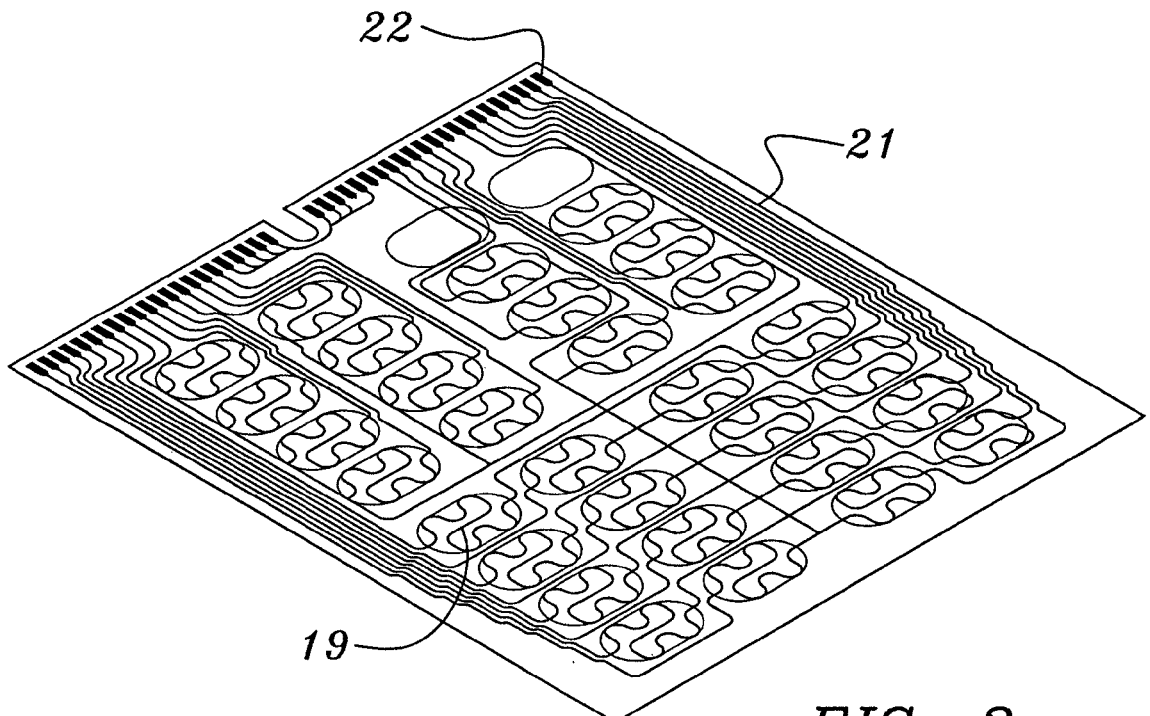
FIG. 3 depicts the blister package without its cardboard backing.

The overall electrical wiring layout for identifying access and removal of product from blister cavities for blister package 10 is illustrated in FIG. 3. A simple electrical circuit comprised of the circuit switches 19, wirings 21 and contacts 22 is etched or placed onto the backing material. The circuit is comprised of conductive material that has one contact end 22 at a first position and a second contact 22 at a second location of the contact region 16 of the blister package. Each blister opening 17 comprises its own similar circuit. The contact region 16 of the blister package preferably includes the contact members 22 for all the different cavities of the blister package. The circuit and its contact members are used for the purpose of determining whether a medication is still in its blister cavity or protrusion. A current or charge can be applied to one contact end and if the current passes to the second contact end, it can be ascertained that the backing is not broken and the medication is still in its protrusion. Conversely, if the medication is taken out, the opening is broken or torn which breaks the circuit and the current or charge will not pass through to the second contact end.

Figure 4:
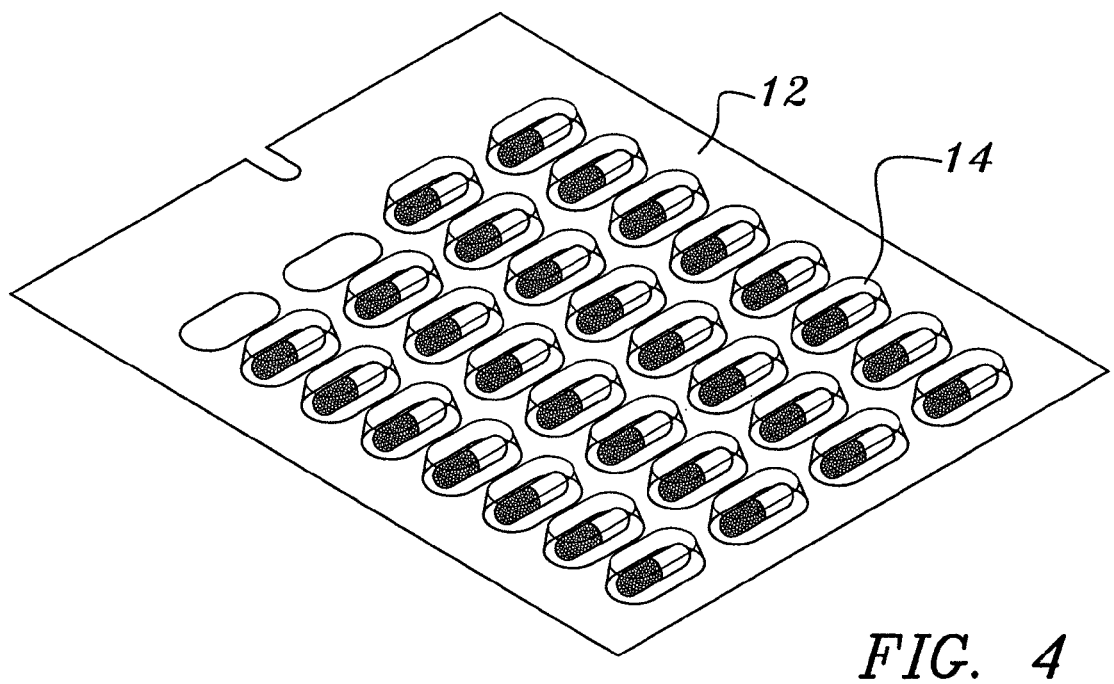
FIG. 4 illustrates an alternate embodiment of the blister package.
Figure 5:
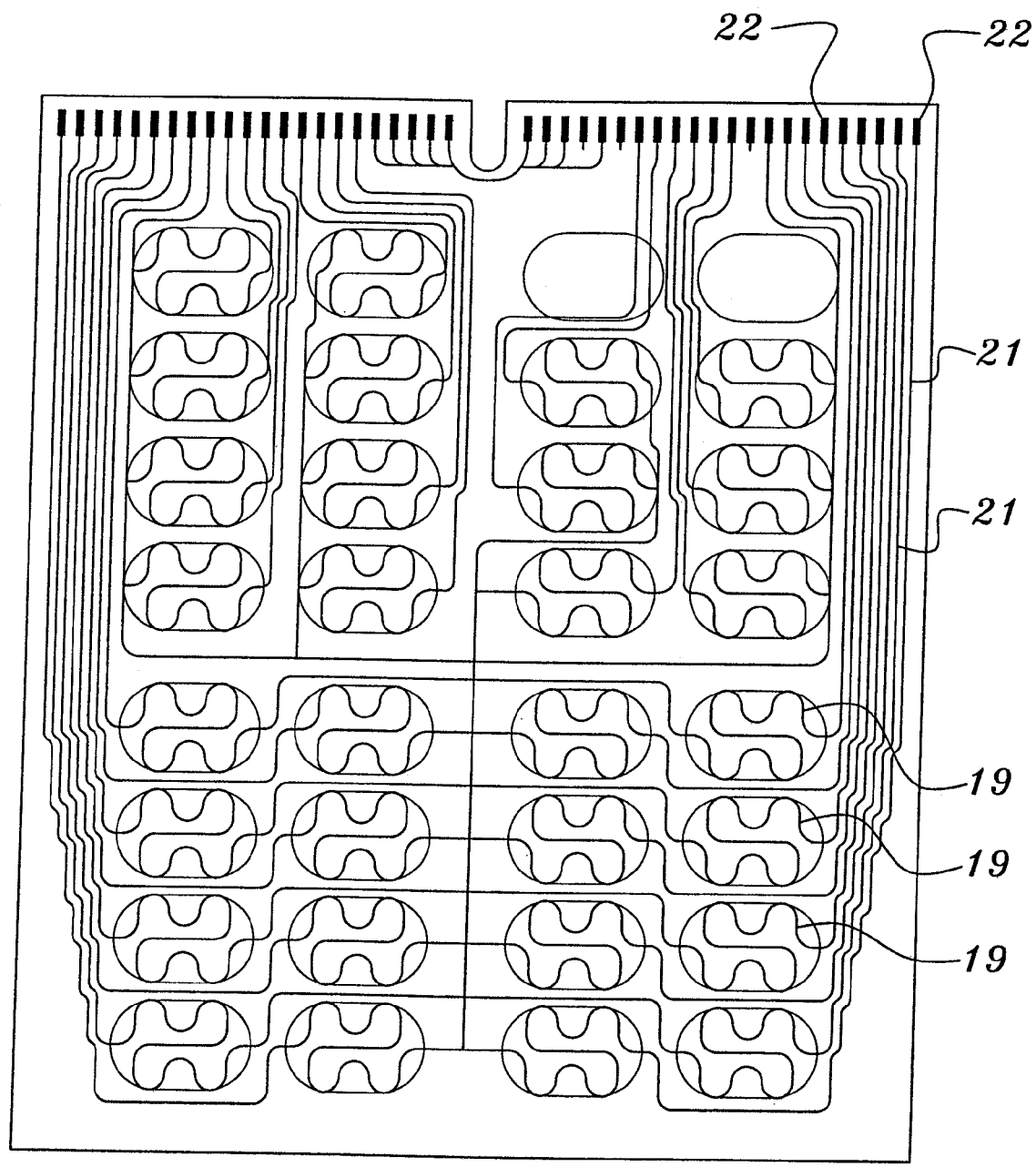
FIG. 5 is a schematic posterior plan view showing the electrical wiring layout of the medication blister package of FIG. 3.

FIG. 4 illustrates the clear plastic sheet 12 with blister protrusions 14 of the blister package 10 without a contact side and without the cardboard cover sheets. FIG. 5 illustrates an alternate view of the circuitry described in FIG. 3, which shows the circuitry in greater detail.

Figure 6:
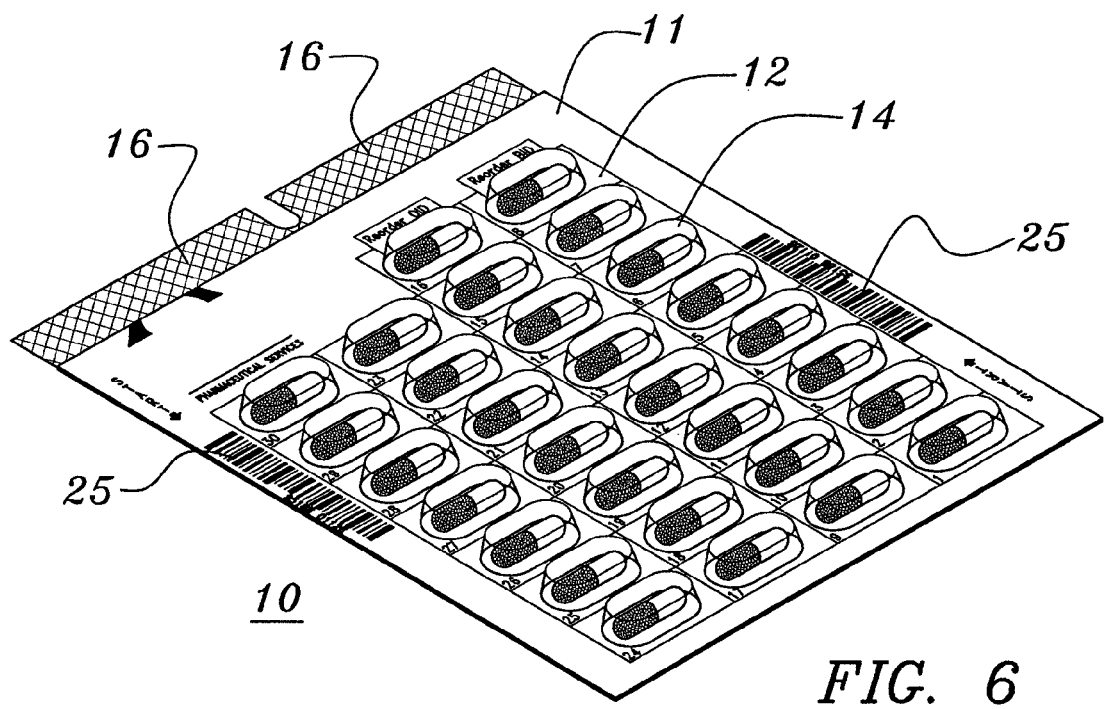
FIG. 6 displays a blister package with a bar code.
Figure 7:
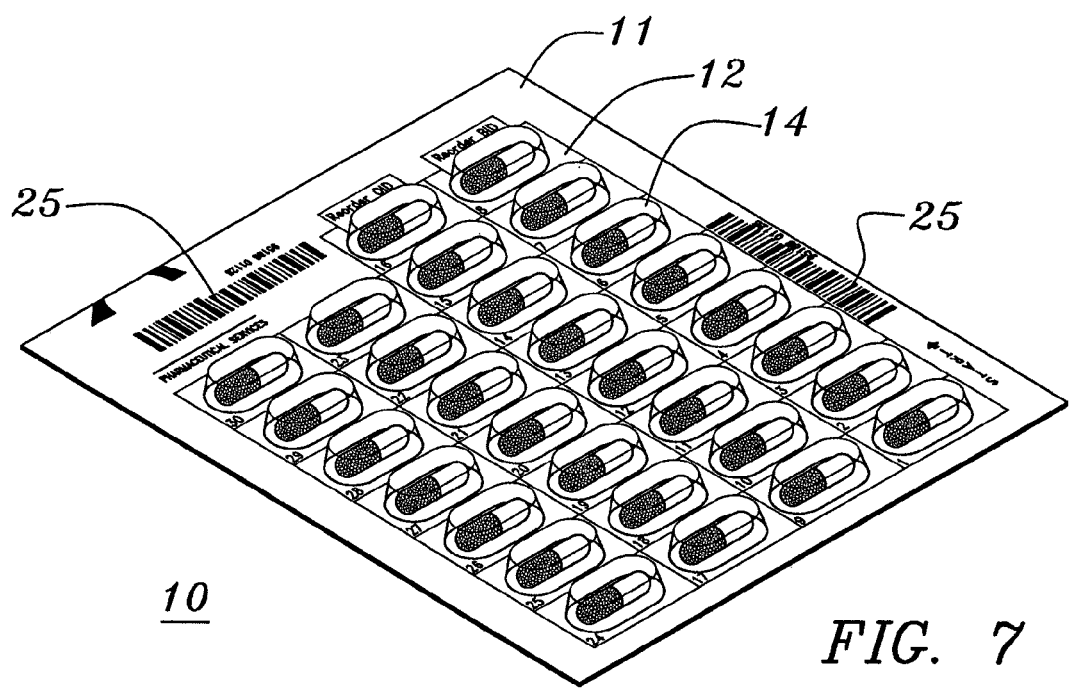
FIG. 7 presents a blister package with a bar code but without a current contact side.

FIGS. 6 and 7 also show alternate views exemplary embodiments of the blister package 10. In FIG. 6, the blister package 10 also comprises barcode 25 or a similar information storage means on one or more sides of the blister package. Those skilled in the art will appreciate that the bar code may be placed at any location on the package. FIG. 7 presents the same blister package 10 with the barcode 25 or a similar information storage means but without the electrical contact region 16. The barcodes 25 and other similar information recording means may contain information such as patient specific information, medication dosage information, medication expiration dates, medication interactions, or any other information as is known to those of ordinary skill in the art. The information on the barcode is compared to the information about the medication, described below, in order to dispense the desired and correct medication.

Figure 8:
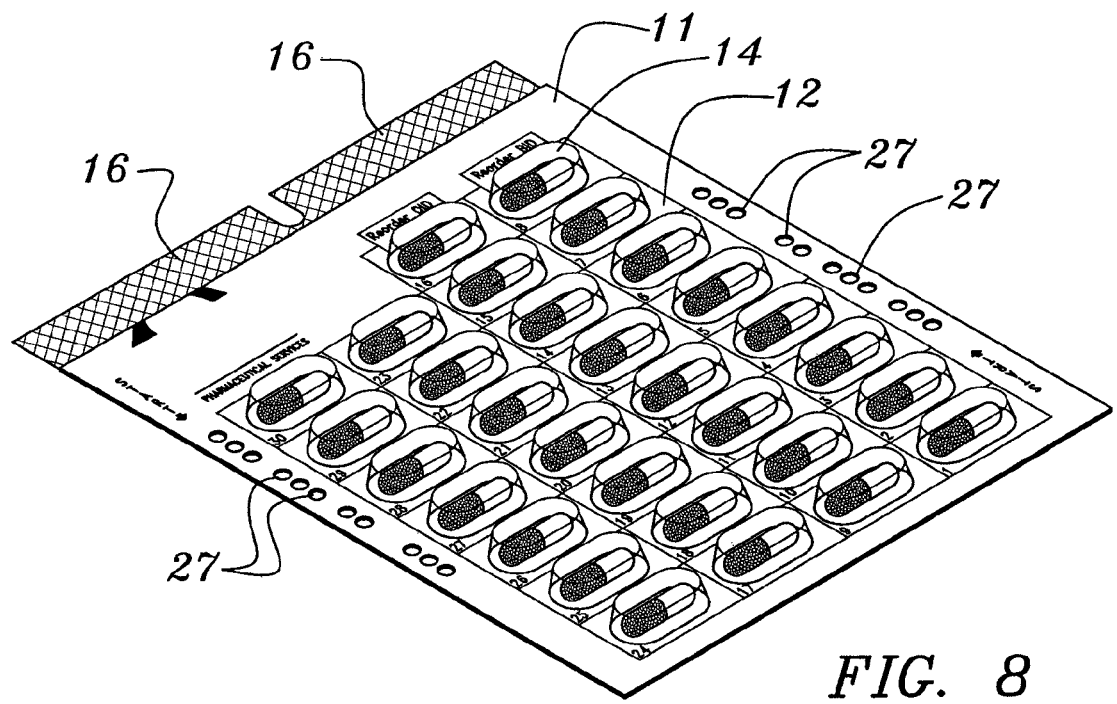
FIG. 8 illustrates an alternate preferred exemplary embodiment of the present invention.
Figure 9:
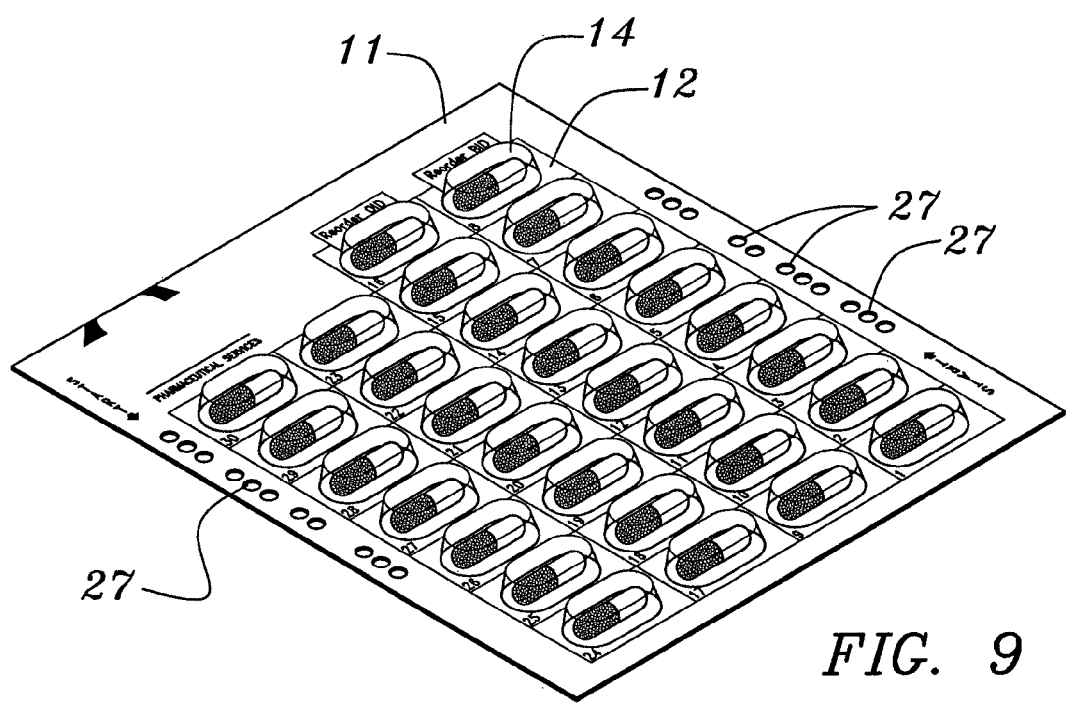
FIG. 9 illustrates an alternate preferred exemplary embodiment of the present invention.

FIGS. 8 and 9 illustrate alternate exemplary embodiments wherein openings or holes 27 on the sides of the blister card member are provided for the purpose of providing information to an optical reader or a mechanical reading mechanism of the package storage distribution and central system of the present invention.

Figure 10:
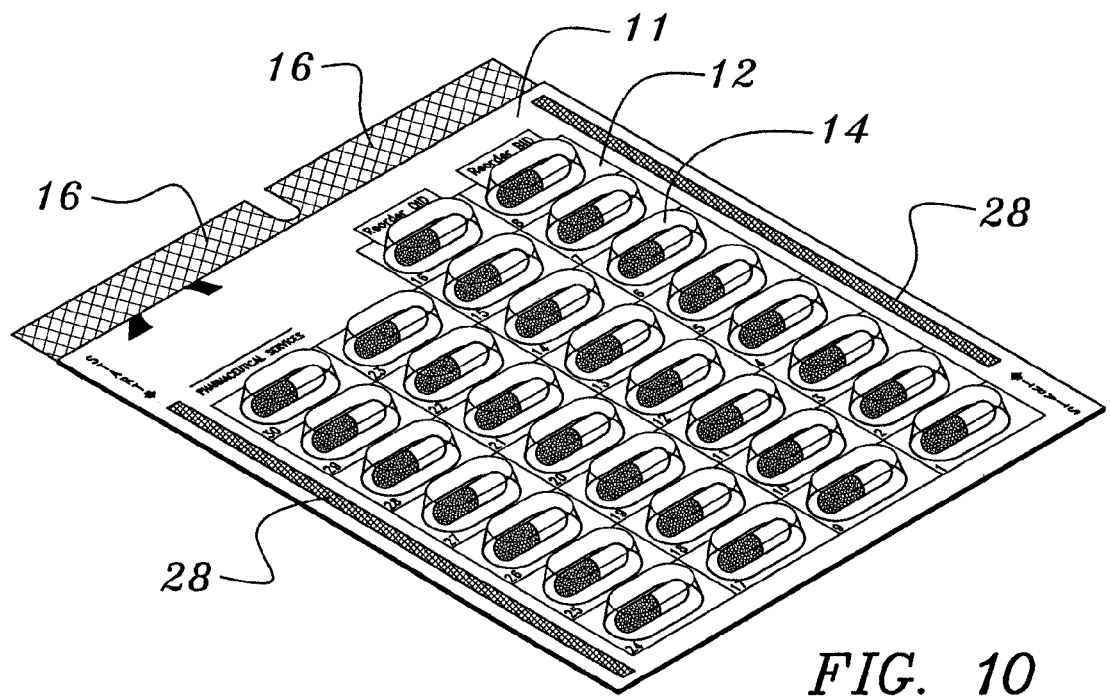
FIG. 10 displays a blister package with a magnetic strip.
Figure 11:
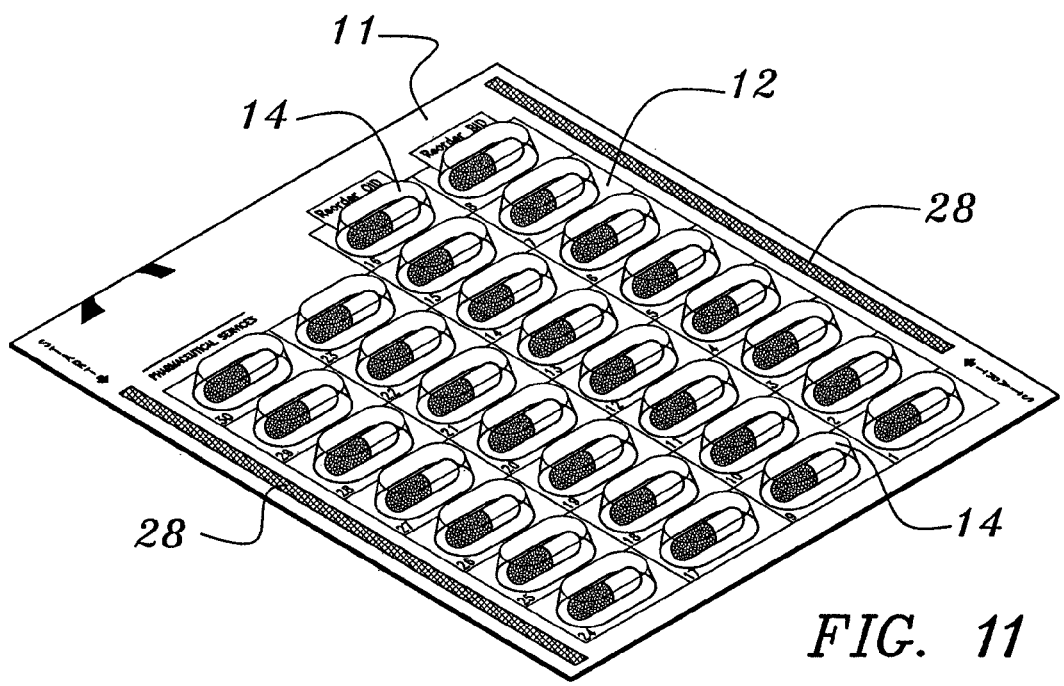
FIG. 11 depicts a blister package with a magnetic strip but without a current contact side.

FIGS. 10 and 11 illustrate other exemplary embodiments of a blister package 10. FIG. 10 illustrates a blister package 10 with an electrical contact region 16 and a magnetic information storage mechanism 28 on one or more sides of the blister package 10. FIG. 11 displays a blister package 10 with the magnetic storage mechanism 28, but without electrical contact region 16. The magnetic storage media 28 can also contain information such as patient information, medication dosage information, medication expiration dates, medication interactions, or any other information as is known to those of ordinary skill in the art. The information on the magnetic storage mechanism can be compared to the information about the medication, described below, in order to dispense the desired and correct medication.

Figure 12:
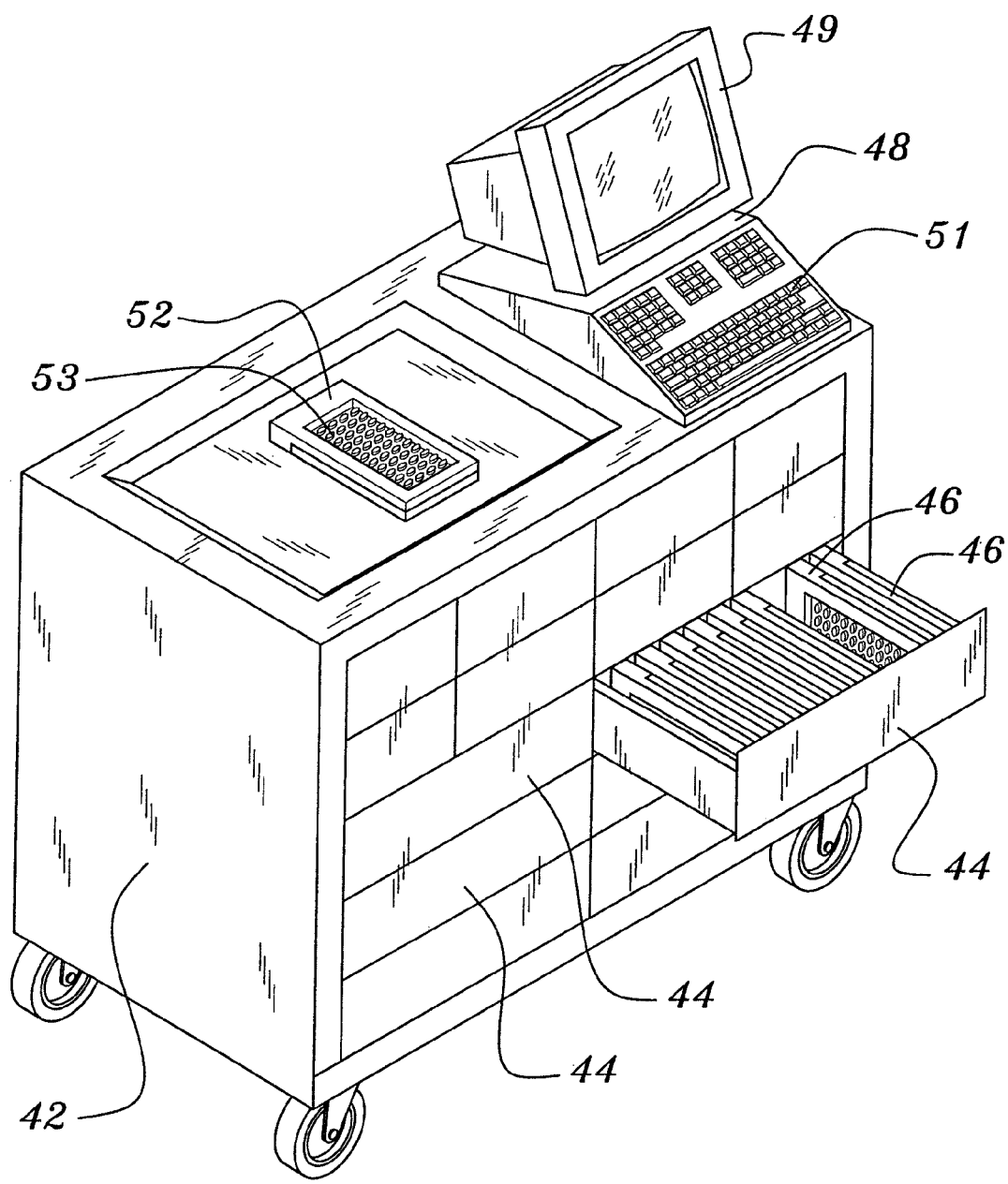
FIG. 12 illustrates an alternate preferred exemplary embodiment of the present invention.

FIG. 12 illustrates a preferred exemplary embodiment of the present invention wherein a mobile pharmaceutical storage, delivery, and access control system of the present invention is described generally at 40. In accordance with this alternate preferred exemplary embodiment of the invention, a wheeled cart or cabinet 42 preferably includes a number of accessible or slidable drawers 44 within which preferably a plurality of individual solid pharmaceutical product package blister cards and/or frames containing solid pharmaceutical package blister cards 46 are provided.

Additionally, in accordance with the preferred exemplary embodiment, a computer 48 preferably includes a display screen 49 and a keyboard 51. In the preferred exemplary embodiment of the present invention, the computer 48 is used for the purpose of accessing patient information preferably related to medication dosing requirements. Those skilled in the art will appreciate that the mobile cart 42 may include a memory such as a disk drive or EEprom memory within which data concerning medication distribution to a variety of patients is stored.

In an alternate embodiment the information regarding patient dosage may be accessible through a wireless network. Regardless of whether the patient information is stored in the cart temporarily or whether the information is accessed via a wireless or wired network, the system advantageously provides a user with quick and convenient access to patient records concerning medication requirements. In accordance with the preferred exemplary embodiment, when a particular patent is to receive a specific dose of a particular medication, the user receives access to the patient record via the computer 48 by selecting a particular patient name in order to identify medication for distribution.

The system preferably unlocks the appropriate drawer 44, and in a preferred embodiment automatically opens the drawer 44 containing the prescribed solid pharmaceutical product. In accordance with the preferred exemplary embodiment of the invention, one of the solid pharmaceutical product package blister card members and/or frames containing a blister card is removed as shown by the frame 52 containing blister package card 53 that is located on the top of the medication distribution cart 42. In the preferred exemplary embodiment the individual using the distribution systems and methods of the present invention is able to easily access the medication through the blister package card and return the blister package card and/or frame member 52 to its appropriate slot in the mobile pharmaceutical storage device 42.

Figure 13:
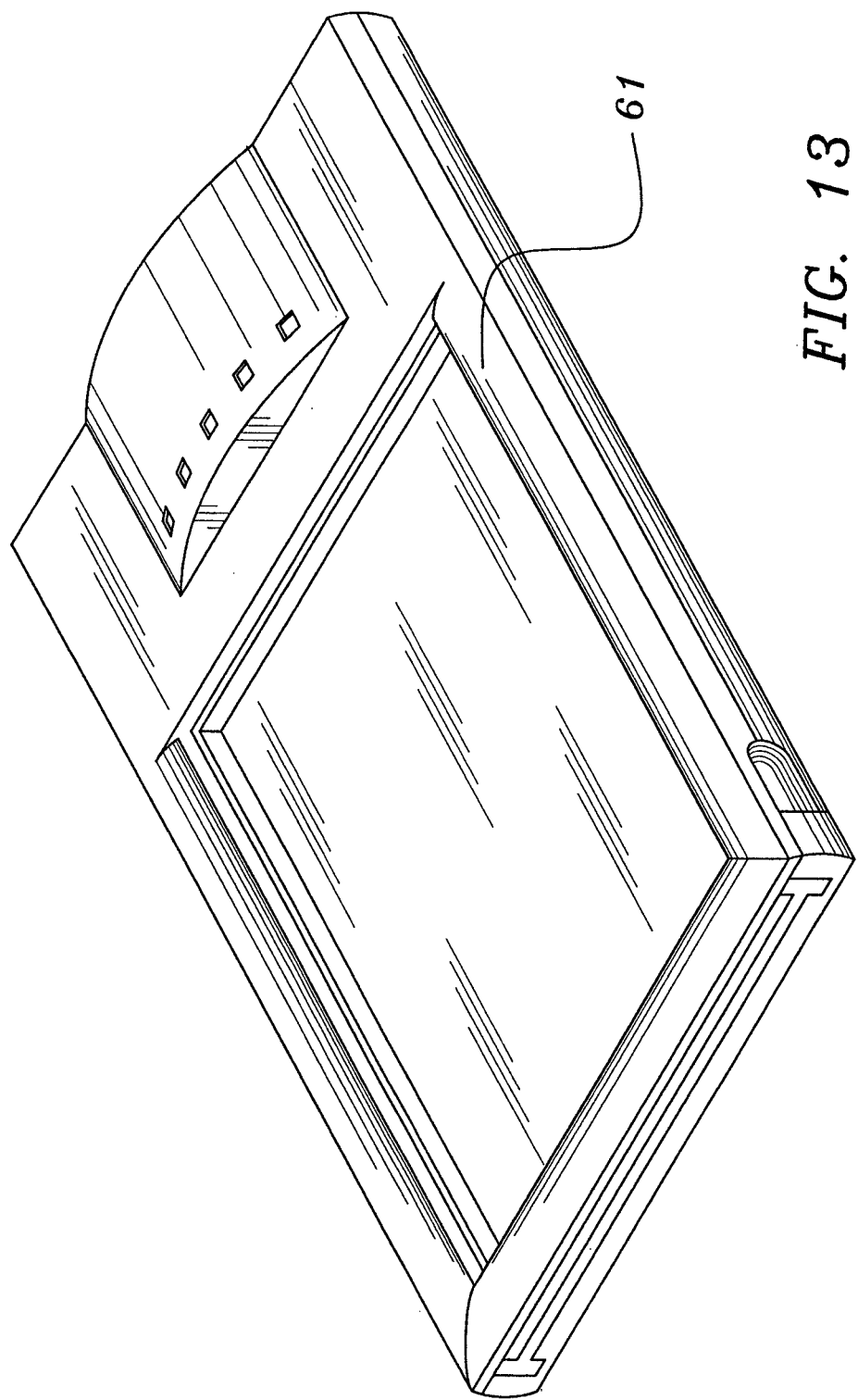
FIG. 13 illustrates an alternate preferred exemplary embodiment of the present invention.

FIG. 13 illustrates an alternate embodiment of the frame 61 which is comprised of a frame having a central location 62 surrounded by the frame 61 for receiving a blister package card member (not shown) which is compatible with the distribution cart of the present invention.

Figure 14:
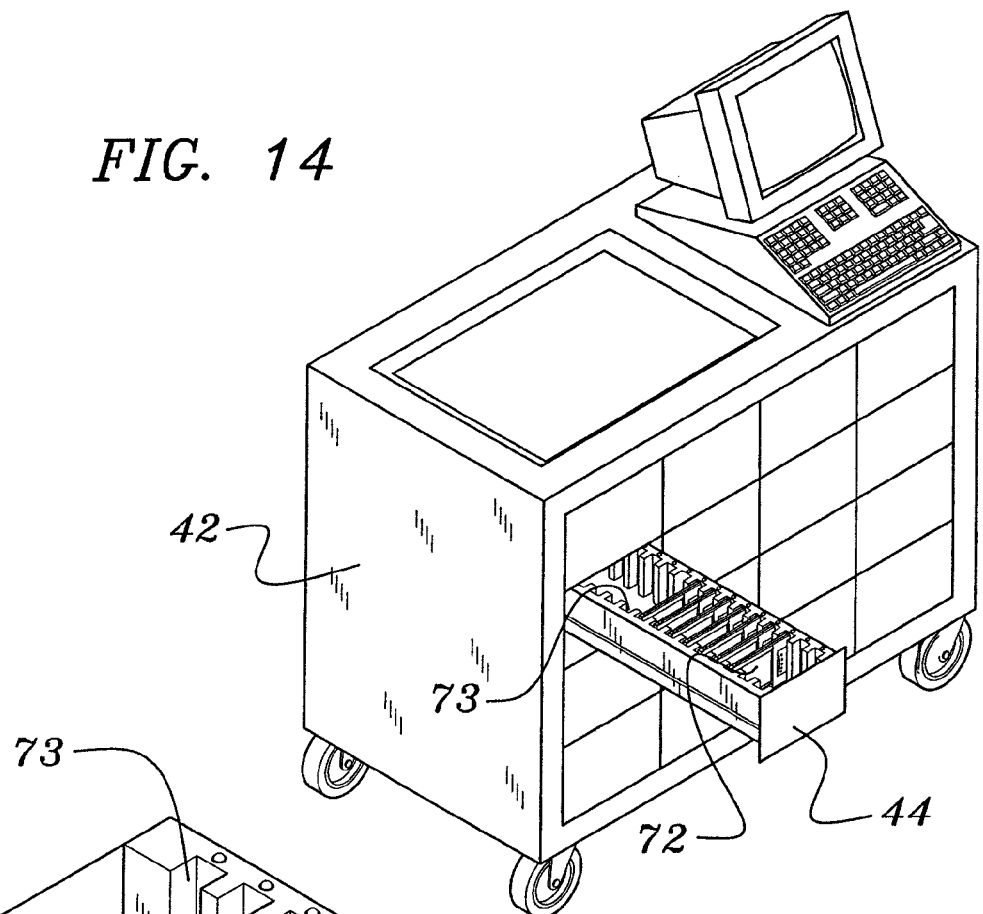
FIG. 14 illustrates an alternate preferred exemplary embodiment of the present invention.

FIG. 14 illustrates an alternate embodiment of the cart wherein the drawers 44 of the cart are compatible with frame member 72. The frame member 72 illustrated in FIGS. 14 and 15 are the same frame members for containing a solid pharmaceutical product package card member as illustrated, for example, in FIG. 13.

Figure 15:
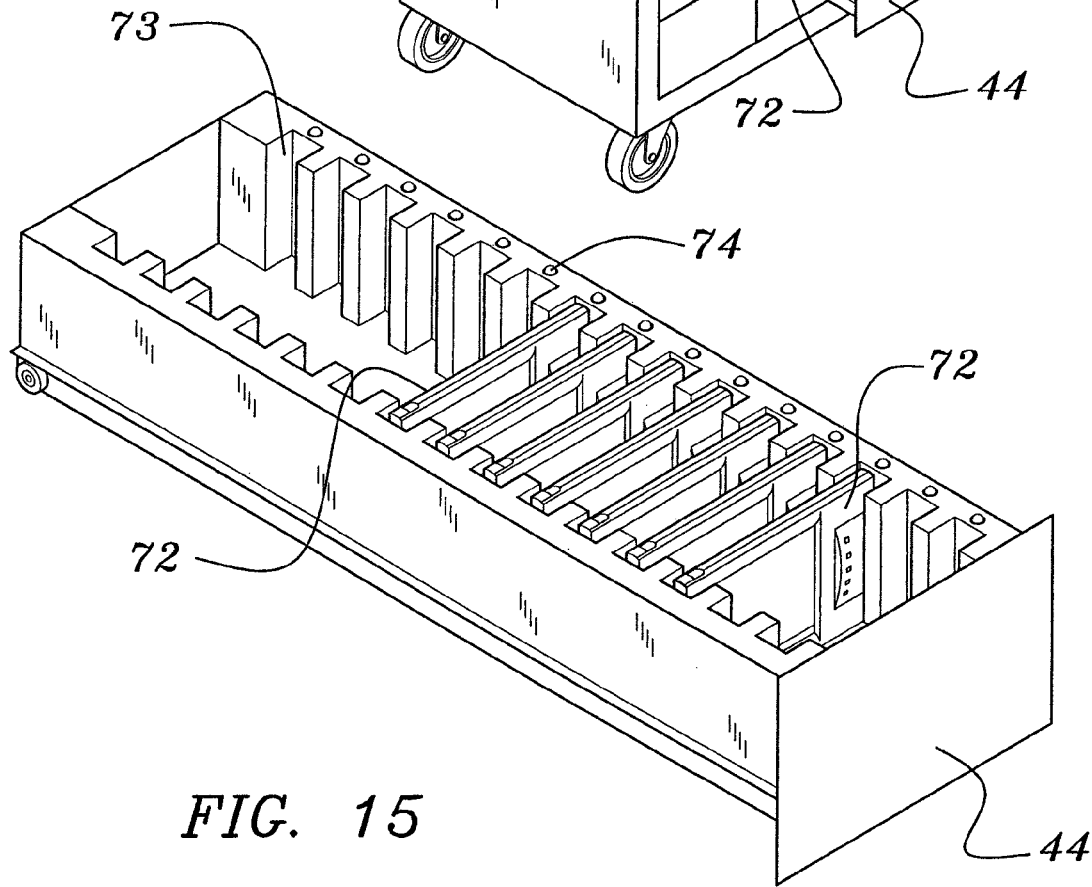
FIG. 15 illustrates an alternate preferred exemplary embodiment of the present invention.

In this alternate embodiment of the present invention, the drawer 44 illustrated in FIG. 15 which is the same as the drawer 44 illustrated in FIG. 14 preferably includes a plurality of slots 73 for receiving an individual frame member 72 and preferably each of the slots is associated with a corresponding light 74 that is embodied as a light emitting diode which may be used for identifying the appropriate slot within which a particular medication or patient prescription package may be found.

In accordance with this alternate preferred exemplary embodiment of the present invention, the medicine distribution cart 42 preferably includes a computer system for providing access to a particular drawer 44 and the particular prescription for distribution to a patient that is required is advantageously identified through automatic illumination of the appropriate light 74.

In accordance with these preferred exemplary embodiments, it is also preferred that a product package card reading mechanism is provided so that the machine is able to discern and confirm the contents of the package when it is inserted and/or removed from a particular slot.

The reading mechanism that is associated with the medical product distribution system is preferably embodied as a barcode reader, text reader, magnetic stripe reader, RF ID tag interface device, or any other reading mechanism that may be used for the purpose of reading information from the blister package card and/or the frame containing the card member.

In the preferred exemplary embodiment, the reading mechanism is preferably incorporated directly into the drawer containing the medication so that information on the pharmaceutical blister package card and/or the frame containing the card can easily read during insertion and/or removal from the slot. Accordingly it is preferred that the reading mechanism be secured adjacent to or incorporated with in the slot of the drawer. Those skilled in the art will appreciate that the reader can also be otherwise associated with the medication distribution system so that the user may swipe the reader across the blister package and/or frame upon insertion and/or removal from the slot. It is merely preferred that the device be incorporated such that the reading occurs automatically during insertion and/or removal of the card.

Advantageously, by providing the blister package card reading mechanism, the computer controller is able to automatically identify the location of a particular product package. This enables the system to readily identify the drawer and slot within the drawer when filling a prescription. Accordingly, the user is able to access a particular patient record with the computer in order to identify a prescription. The system will thereafter automatically identify the location within the card where the prescribed medication or medications are located. This is preferably done sequentially so that the individual administering the medications can ensure that each has been appropriately administered to the patient.

As noted, this is performed preferably by automatically unlocking a selected drawer containing the desired pharmaceutical and illuminating a light associated with the appropriate slot of the drawer containing the medication. This is particularly advantageous because the system is able to automatically identify the appropriate location of the medications for administration even in those circumstances where the user has removed more than one blister package card and/or frame containing the card from the distribution system. Regardless of where the card is reinstalled into the drawer, the system will automatically identify the location and store this information. Even if the card is inserted into a different location from its original position the system will be able to automatically determine the new location. The system is able to thereby ensure that fewer errors in the administration of medicines occur.

Figure 16:
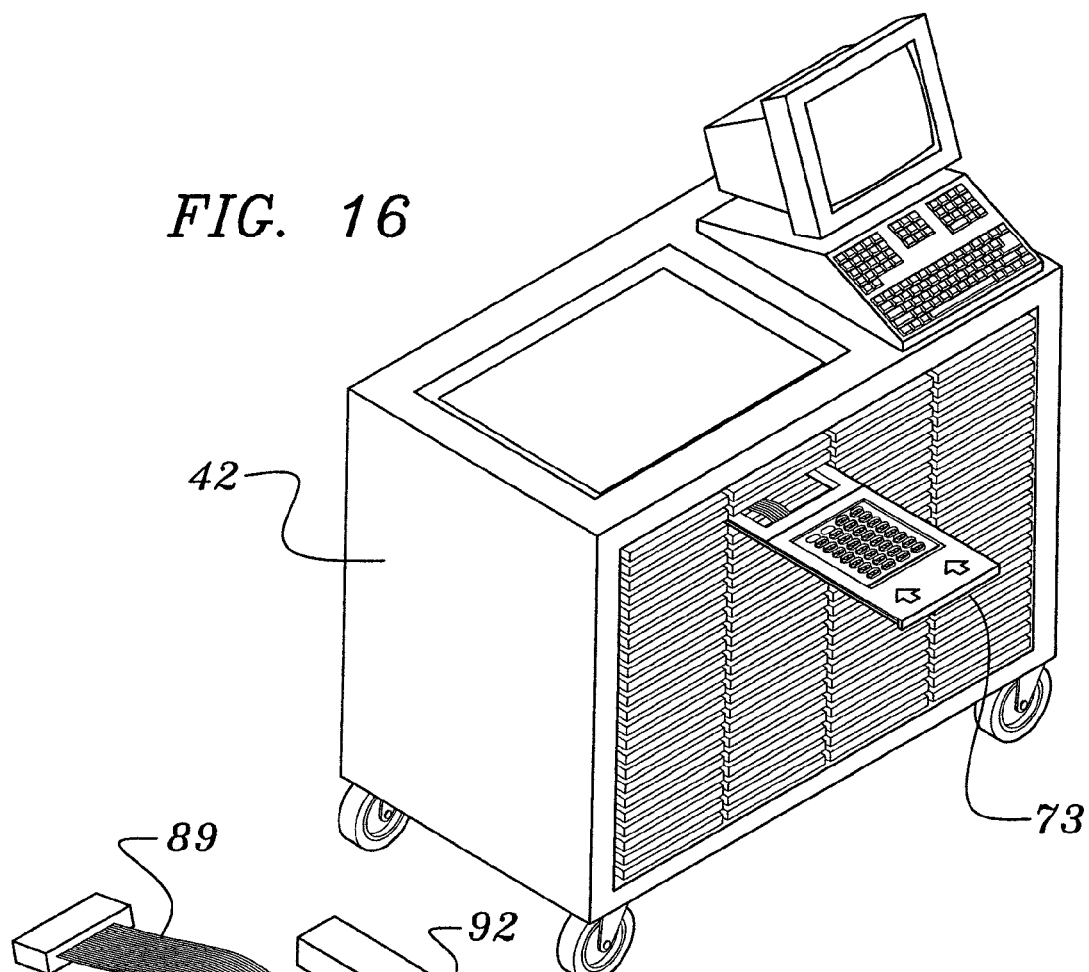
FIG. 16 illustrates an alternate preferred exemplary embodiment of the present invention.

FIG. 16 illustrates an alternate embodiment of the present invention wherein the individual frame members 72 slide in and out of the distribution cart 42 and wherein no drawer is provided for storage of the individual solid pharmaceutical product package card members or frame, containing the card members. Rather, each individual frame 73 slides in and out directly from a corresponding location in the cart. Those skilled in the art will appreciate that the use of LEDs or other lights or signaling mechanisms may be utilized to identify the appropriate solid pharmaceutical package card containing frame within which the desired medication is located.

Figure 17:
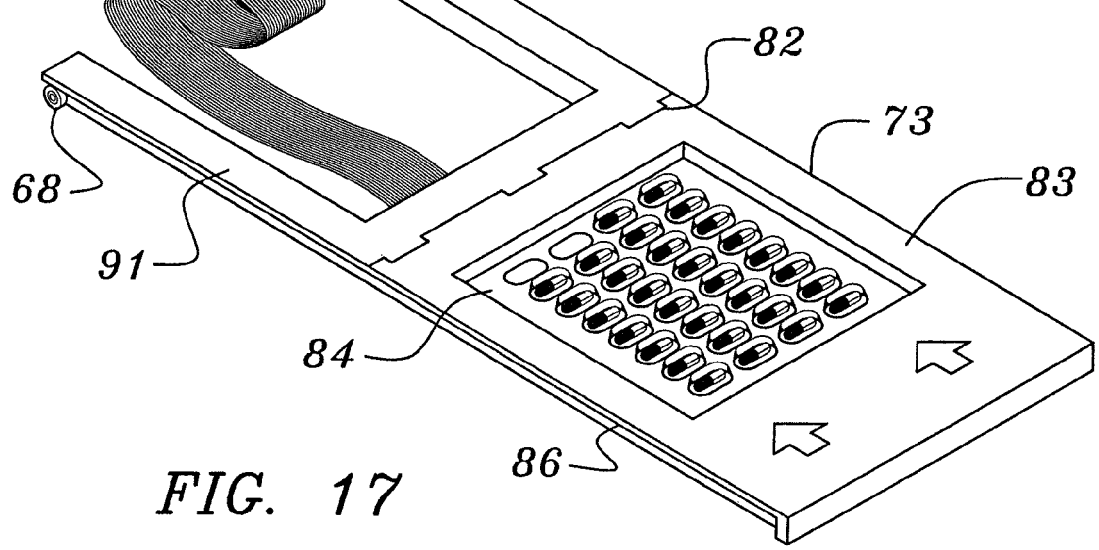
FIG. 17 illustrates an alternate preferred exemplary embodiment of the present invention.

FIG. 17 illustrates the specific arrangement of the frame member 73 that is compatible with the cart of the device illustrated in FIG. 16. As shown in FIG. 17, the frame has a hinge 82 which allows a top member of the frame 83 to close and secure a blister package 84 between the top of the frame 83 and a bottom portion 86. Advantageously this provides good electrical connection with the conductive members illustrated in FIG. 3 and described above, which are located on the blister package card.

In accordance with the preferred exemplary embodiment, a ribbon cable 89 transmits signals to the circuitry from the appropriate drivers of the cart 42, for determining which individual dosage cavities have been utilized. In the preferred exemplary embodiment, wheels 88 are provided on frame displacement support members 91 and 92 that advantageously allow support for the solid pharmaceutical product package frame member while it is partially removed from the cart 42. This is illustrated in FIG. 18 wherein the displacement support members 91 and 92 provide support for the frame member 73.

Figure 18:
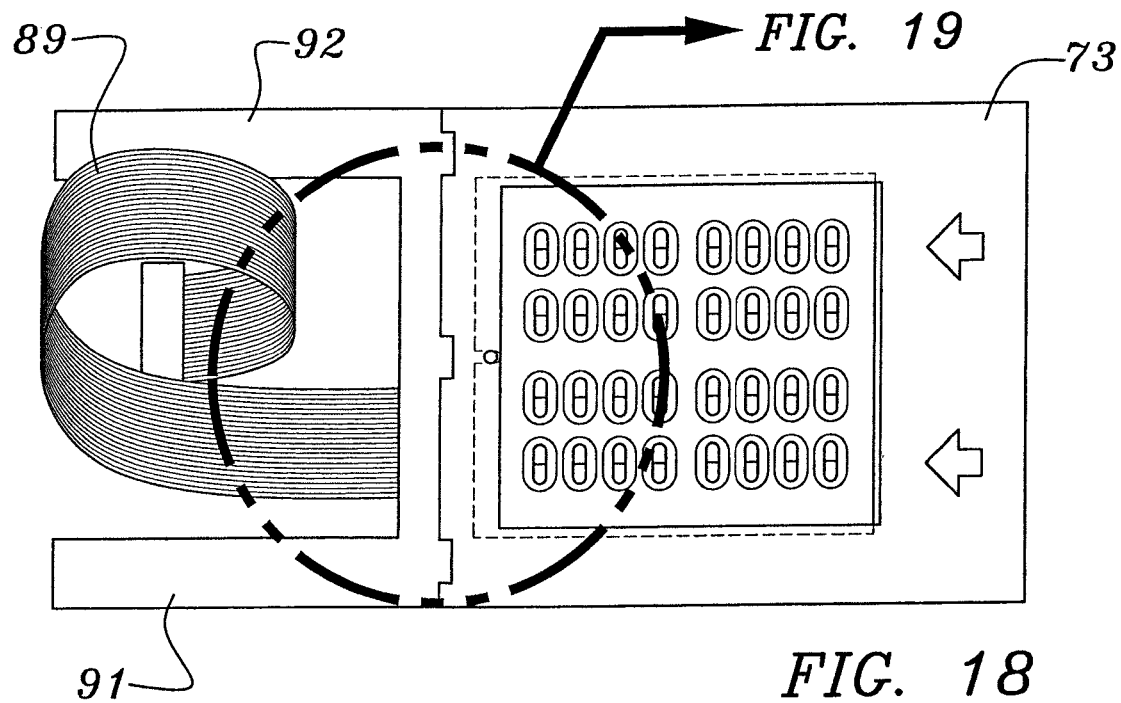
FIG. 18 illustrates an alternate preferred exemplary embodiment of the present invention.
Figure 19:
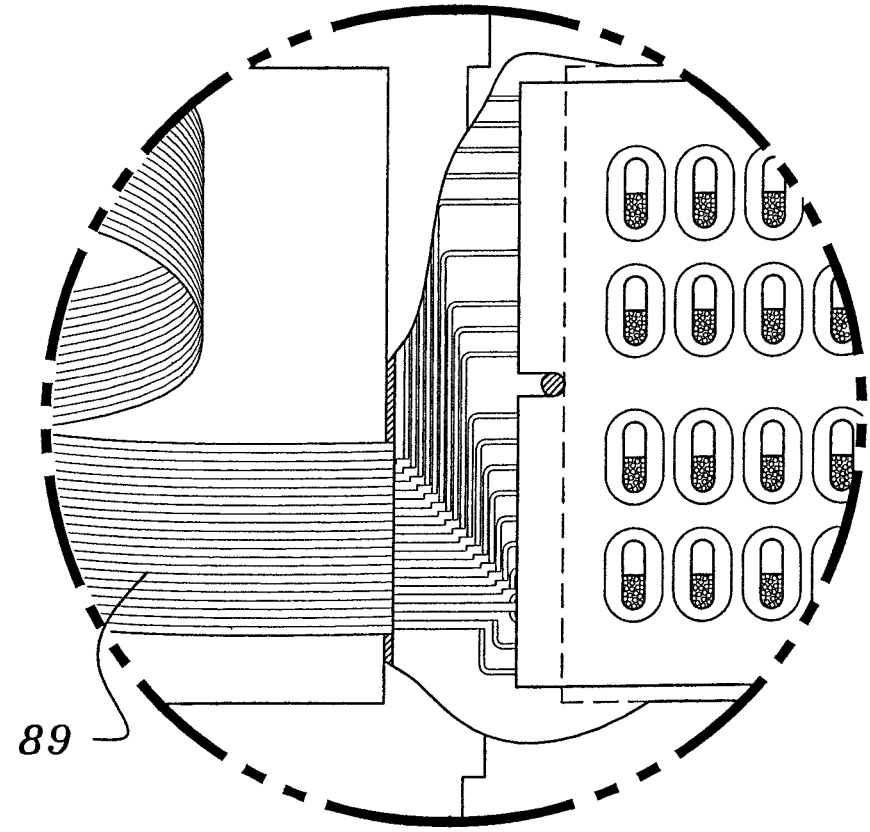
FIG. 19 illustrates an alternate preferred exemplary embodiment of the present invention.
Figure 20:
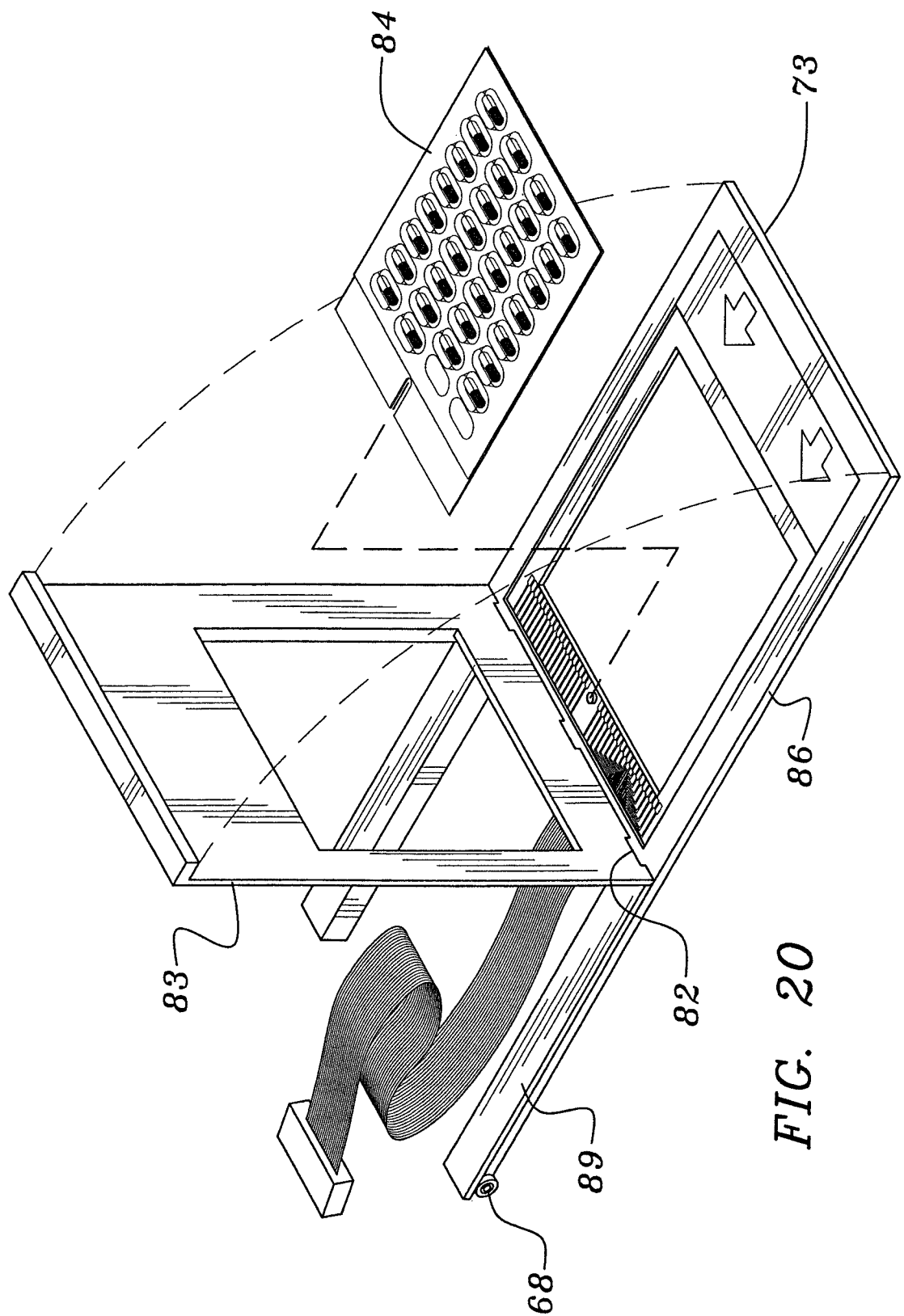
FIG. 20 illustrates an alternate preferred exemplary embodiment of the present invention.

FIGS. 18 and 19 illustrate the connection of the circuitry of the package member to the ribbon cable with the details thereof shown in FIG. 19. FIG. 20 illustrates the opening and closing of the frame on the blister card. As shown in FIG. 20, closing the upper portion 83 over the blister card ensures a good electrical connection.

Figure 21:
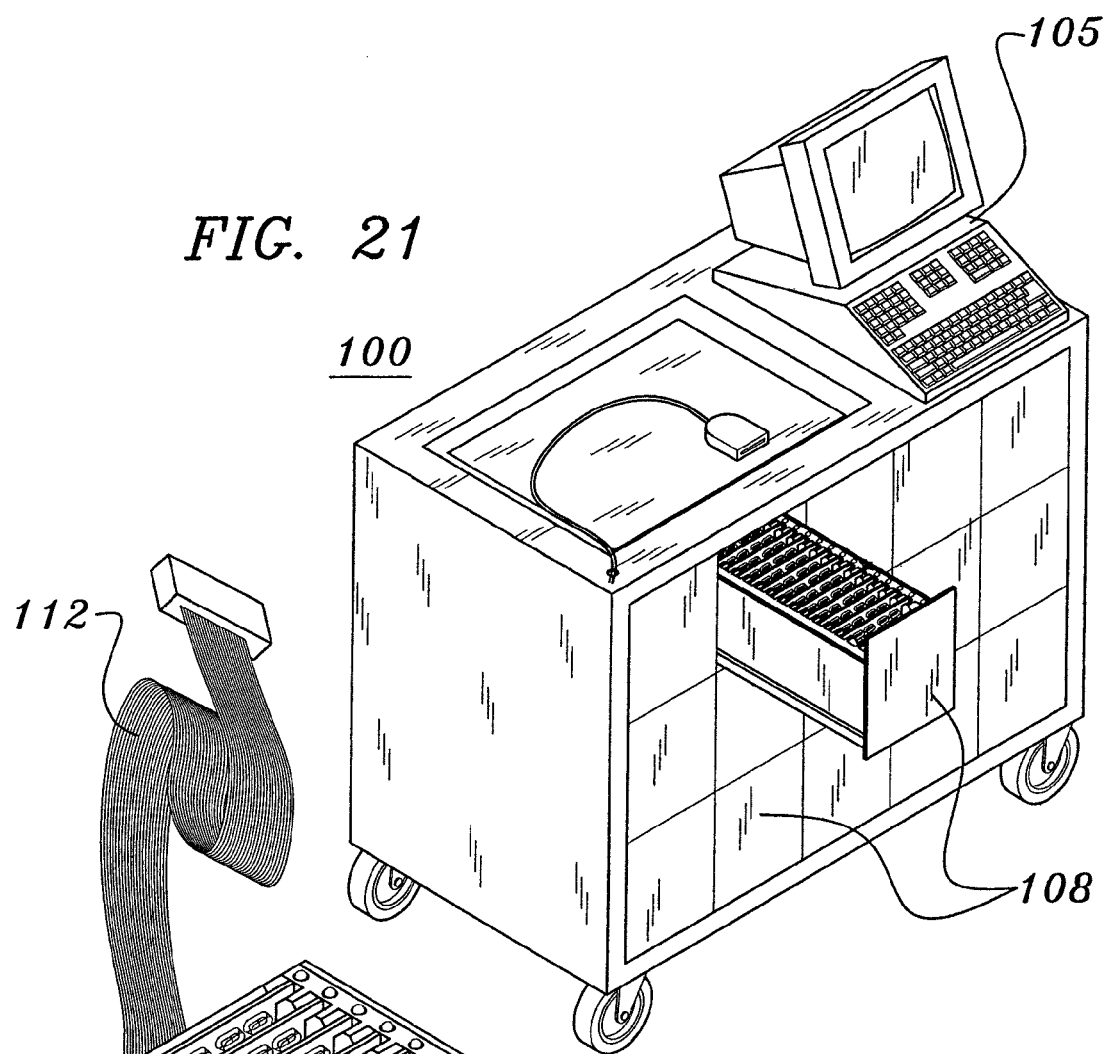
FIG. 21 illustrates an alternate preferred exemplary embodiment of the present invention.

FIG. 21 illustrates yet another alternate preferred exemplary embodiment of the present invention, which is shown generally at 100. In this alternate preferred exemplary embodiment of the invention, the medical information and product distribution system 100 comprises a computer 105. Additionally, any other device which is able to store, retrieve or process patient information, inventory information, prescription information or medication requests, such as a server, a personal digital assistant (PDA), a laptop, or a tablet computer, may also be used. The independent medical information and product distribution system 100 can retrieve a patient's medical history and/or prescription information and communicate the same to the storage/dispenser unit. It should be appreciated by those of ordinary skill in the art that it can process medication requests based on pre-defined requests such as at a specified time, patient name or information as well as communicate with the independent storage device.

Furthermore, the medical information and product distribution system 100 may or may not be part of a hospital management system. It should also be appreciated by those of ordinary skill in the art that medical information and distribution system 100 may perform various other functions not specified here.

The computer 105 of the medical information and product distribution system 100 is preferably connected to an independent storage/dispenser unit 42 via a direct connection, the internet, an intranet, a VPN, a wireless, an infrared or any other communications protocol. By way of example, FIG. 22 discloses a computer placed on top of and directly connected to the independent storage/dispenser unit 42. However, it should be appreciated by those of ordinary skill in the art that each unit or device can perform its function in conjunction with other such units. For example, one storage/dispenser unit 42 may be used with a particular medical information system, a computer, and later be transported to a different location and used in conjunction with a different computer or other medical information device. Such a system provides several advantages over the prior art.

Considerable resources are conserved because individual storage/dispenser units can be purchased without expensive hardware and software medical information or prescription management systems. This also allows the entire automated dispensing system to be highly scalable based on needs and desires. In fact, one storage/dispenser unit may be connected to one or more medical information systems so long as the medical information systems comprise means for communicating with the storage/dispenser unit 42. Finally, even if the medical information system 100 is not operational, the storage/dispenser unit 42 will continue to operate normally.

Figure 22:
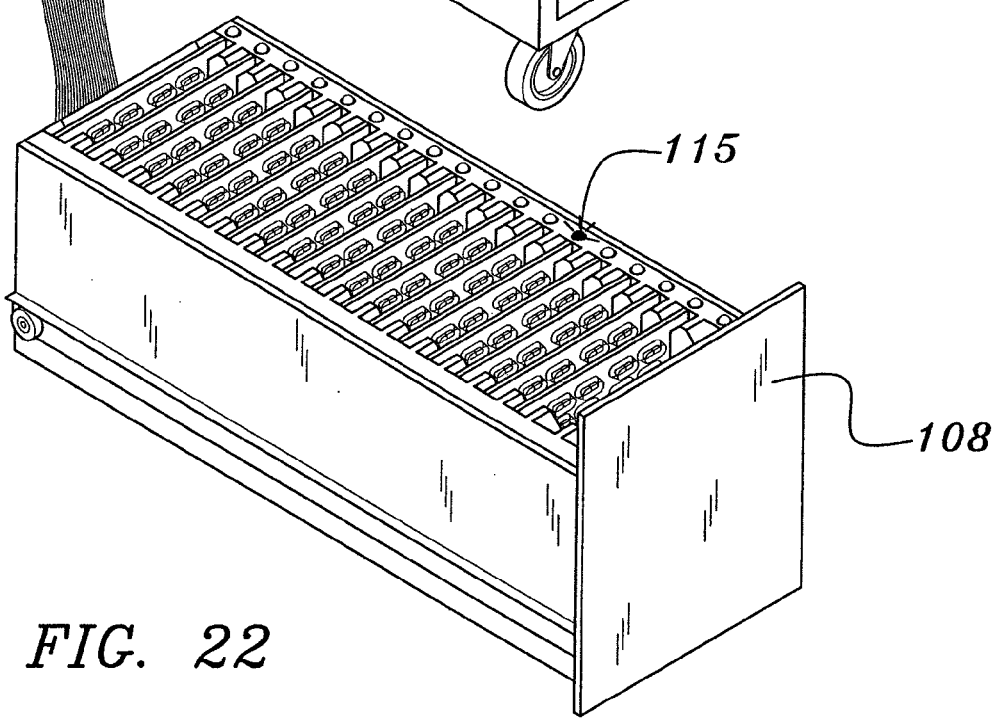
FIG. 22 illustrates the medical information system and the storage dispenser unit.

In the alternate preferred exemplary embodiment of the invention illustrated in FIGS. 21 and 22, the independent storage/dispenser unit 42 comprises a processor, not shown, and several storage compartments 108. A person skilled in the art will appreciate that various types of storage compartments or mechanisms may be used and that the number of storage mechanisms can vary from one to several. The processor, not shown, of the storage/dispenser unit 100 receives information from the medical information system, compares that information with information from the storage compartments 108 and opens the appropriate storage compartment 108. The storage/dispenser unit 100 also comprises an internal relay circuit which is utilized by the processor to automatically open a storage compartment 108.

It will be appreciated by those of ordinary skill in the art that various other mechanisms known in the art may be utilized to automatically open the storage compartments 108. As an advantage, the separation and independent operation of the storage/dispenser system 100 allows it to be smaller and more mobile. For example, FIG. 21 displays the preferred exemplary embodiment of the invention as a smaller storage/dispenser unit that can be transported on wheels 109. Other means of transportation may also be used.

The medicine distribution system illustrated in FIGS. 21 through 24 does not require the frame support for the blister card package as in the embodiments described above. Rather, this embodiment is compatible with individual blister cards without a separate frame support.

With reference to FIG. 22, there is shown a storage compartment 108 of the type used in the preferred alternate exemplary embodiment of the present invention, wherein no frame member is used for securing the blister card. The storage compartment 108 of storage/dispenser unit 100 is connected to the processor via a direct electrical connection 112 such as a ribbon cable, SCSI or IDE connection. It should be appreciated by those of ordinary skill in the art that any connection that allows communication between the storage compartments 108 and the processor may be used. This connection allows the storage compartments 108 to communicate about their contents with the processor and the overall system.

In this preferred exemplary embodiment, once the appropriate drawer has been identified, the slot containing the appropriate blister package and medication is easily identified by illumination of the light. As illustrated in FIG. 22, each slot has an associated light for designating the slot containing the appropriate card. The system determines this location by preferably automatically reading information from the card when it is inserted and/or removed from the slot. This may be done via barcode, magnetic stripe or even a text reading device. The reader may be built in as shown, or manually swiped across the card as noted above.

Figures 23, 24:
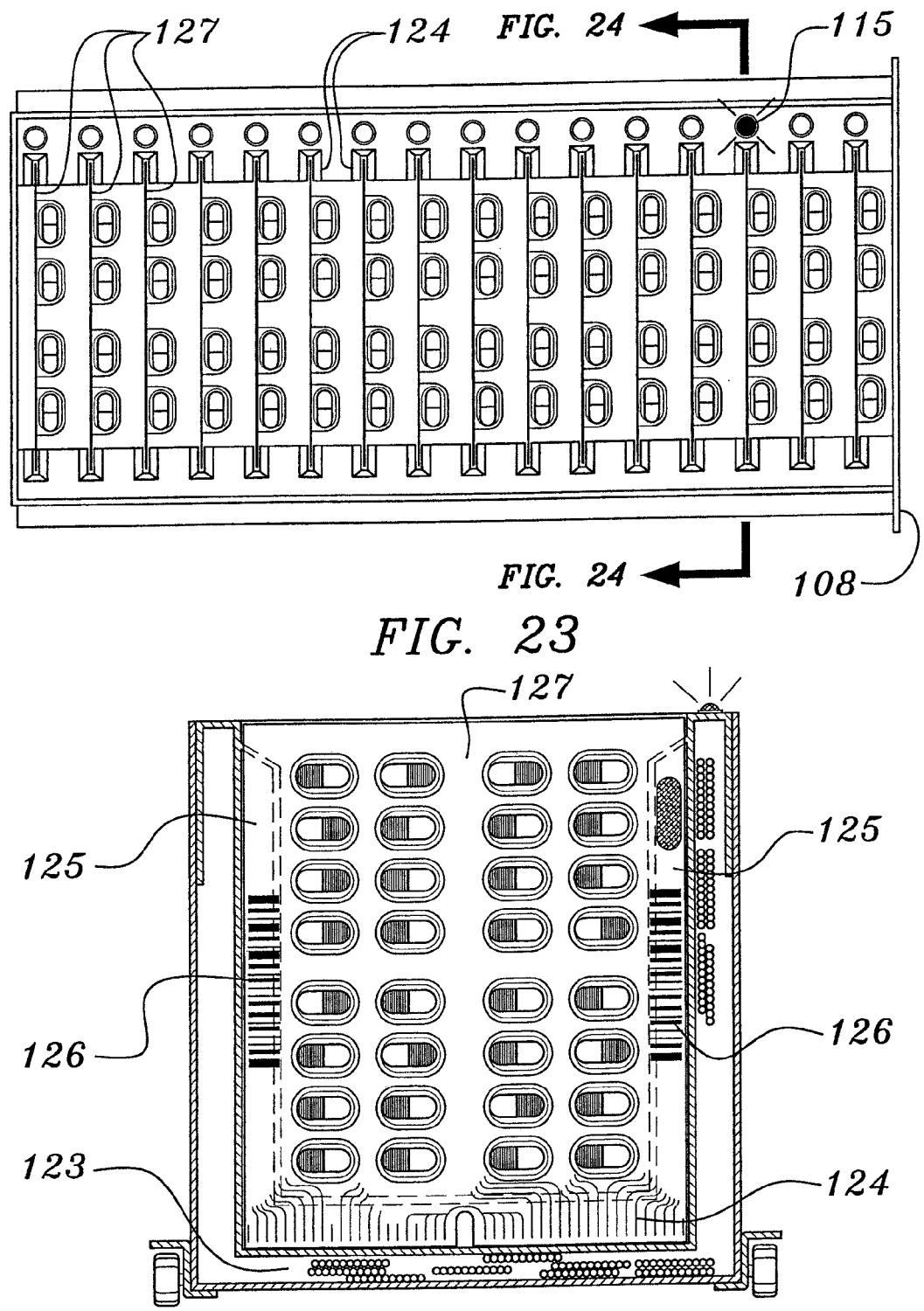
FIG. 23 displays a storage compartment.
FIG. 24 shows a top view of the storage compartment.
Figure 26:
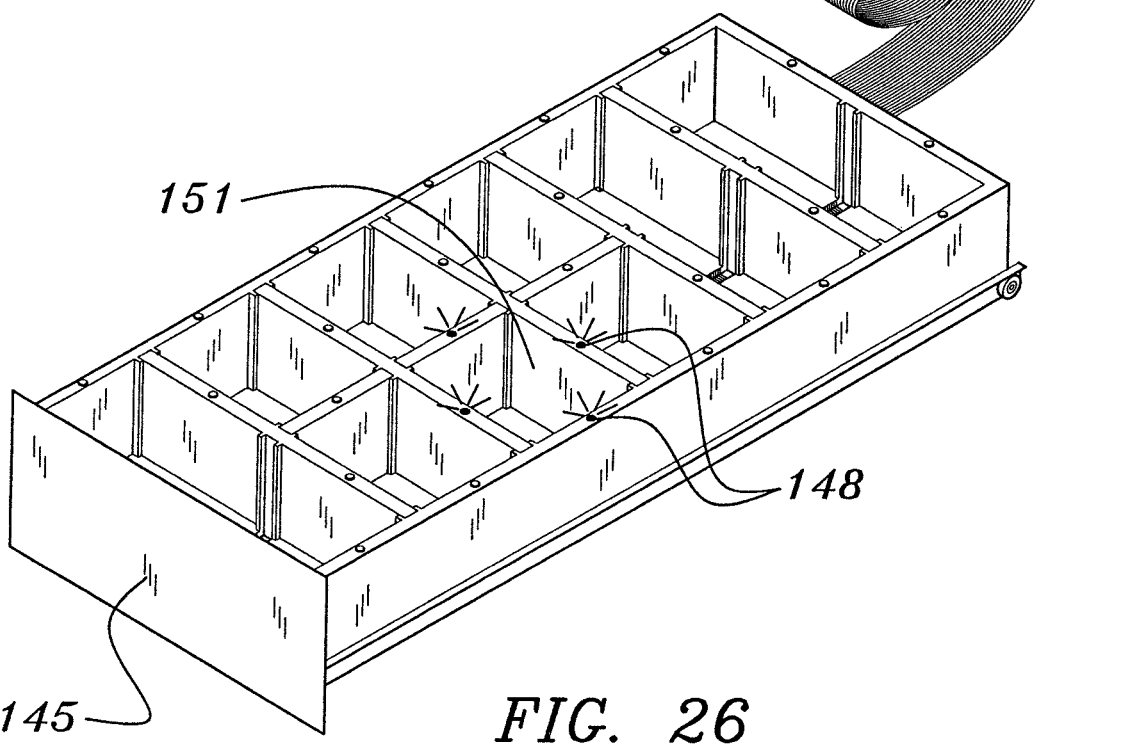
FIG. 26 illustrates an alternate preferred exemplary embodiment of the present invention.

FIG. 23 displays a top view of the storage compartment 108 with its cross-section displayed in FIG. 24, wherein individual blister cards are directly stored in the slots of the storage compartment. The light 115 identifies the appropriate slot. Referring now to FIG. 26, in the preferred exemplary embodiment of the invention, the storage compartments 108 comprise a medication package receiver slot 123 to receive the contact end side 124 of the blister package 127. Additionally, individual storage slots 129 may also comprise information readers 125 for reading the barcode 126 or magnetic storage media locations on the blister packages. As noted, this may also be a text reader.

However, it should be appreciated that either contact ends or information storage methods such as barcodes/magnetic devices may not be present on the blister package 127 for storage in the storage compartment 108, which may or may not include the blister medication package information reader mechanism 125.

In the preferred exemplary embodiment, the medication package receiver 123 comprises a device that can place a charge or current on a first contact end of the circuit on the blister package and measure the charge or current passing to its associated second contact end. If the current or charge is detected at the second contact end, the storage compartment and consequently the storage device can determine whether the opening of an individual medication or pill cavity has been opened and whether the medication or pill is still present in its package. On the other hand, if the current or charge is not detected at the second contact end, the individual opening has been opened and the medication or pill is no longer in the package. This information, the presence of charge or current at the second contact end, is communicated to the processor of the storage/dispenser unit and compared with the information for a desired medication from the medical information system 100. The information reader 125 such as the magnetic or barcode reader reads and conveys the information such as the name and dosage of the medication in the blister package. Since the information is obtained from the blister package itself, the system significantly reduces such problems as administration of wrong medication and mistreatment thus allowing health care providers to efficiently and correctly administer appropriate care.

In operation, a user may retrieve prescription information about a particular patient. In order to obtain the actual medication, the medical information system communicates with the storage/dispenser unit to check whether that desired medication is available. The storage/dispenser unit previously received information detailing which products are contained within the storage compartments of the storage/dispenser unit about their locations. The storage compartment determines whether the medication is available or unavailable by using the information reader and/or the contact end reader and conveys the information back to the processor. If the medication is available, the storage device processor then automatically opens the storage compartment and turns on the indicator to specify the specific blister package.

Figure 25:
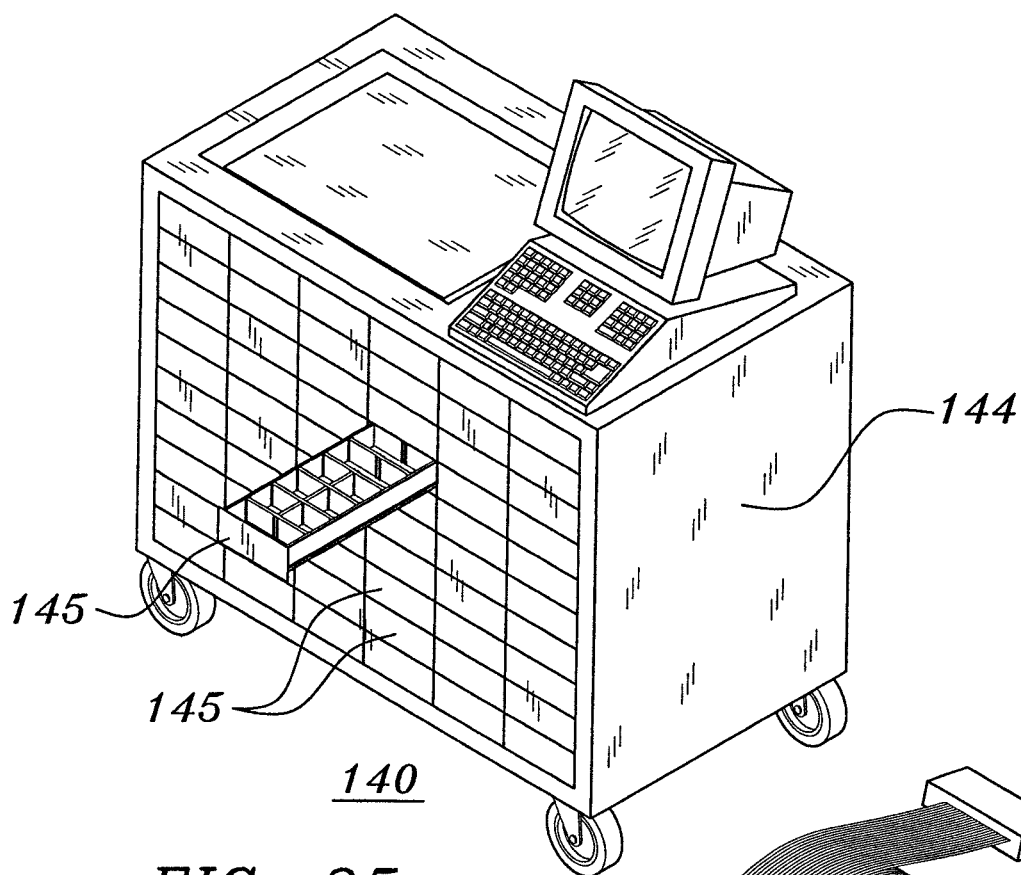
FIG. 25 displays a cross section of a storage compartment with a medication blister package.

FIGS. 25 and 26 illustrate another alternate preferred embodiment of the present invention which is shown generally at 140. In this embodiment, preferably a mobile cart 144 with individual drawers 145 is provided. Additionally, a computer and processing system selectively provides access to the individual drawers within which solid pharmaceuticals that have been prescribed for patients is provided.

FIG. 26 illustrates the specific cavities within a drawer 145 that are used for receiving and storing the solid pharmaceutical products.

As illustrated therein, lights 148 may be used to illuminate the perimeter of a cavity 151 within which a particular solid pharmaceutical product has been stored. This merely illustrates an alternate embodiment wherein no blister package or frame is required.

Figure 27:
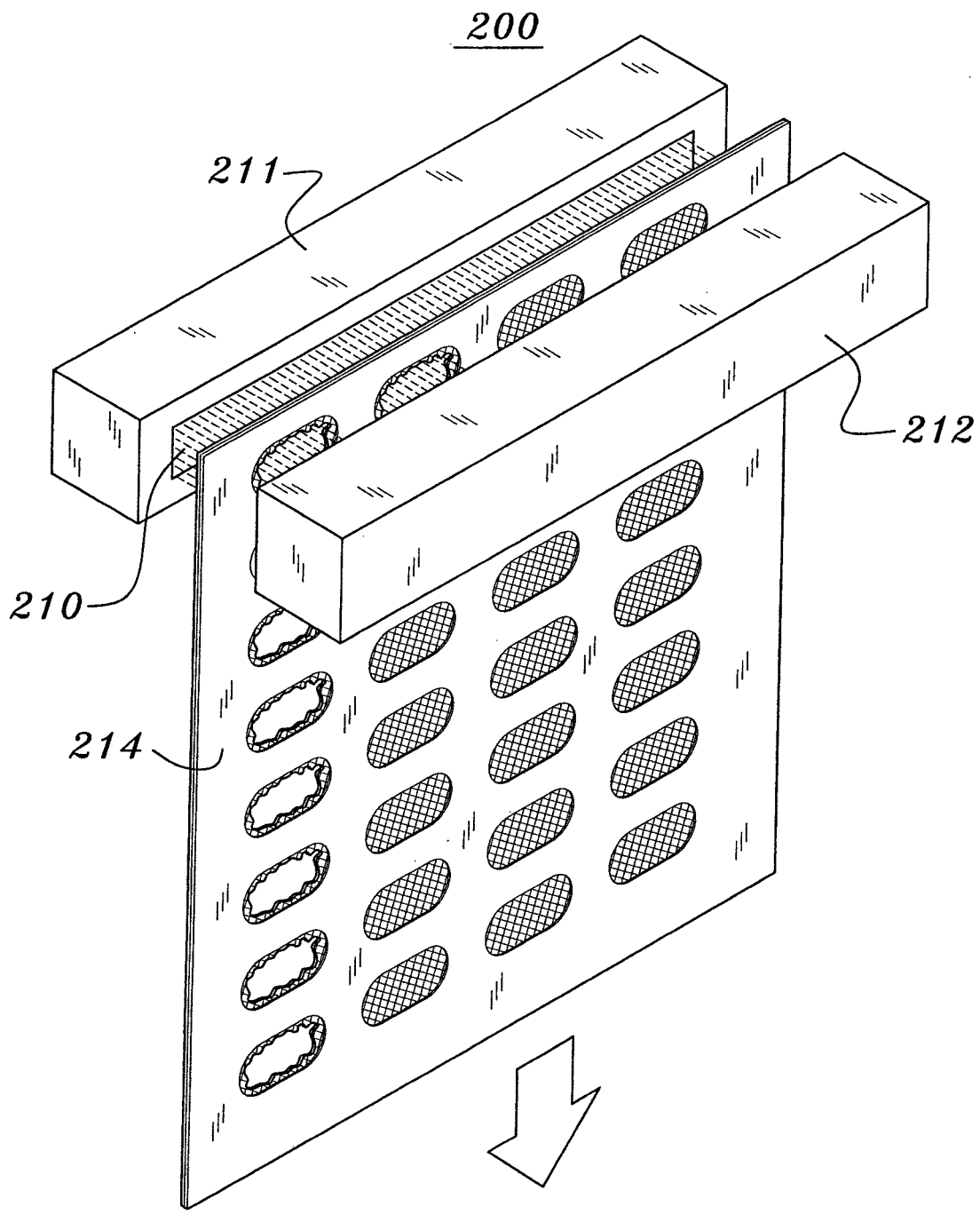
FIG. 27 illustrates an alternate preferred exemplary embodiment of the present invention.

FIG. 27 illustrates yet another alternate preferred exemplary embodiment of the present invention which is shown generally at 200. In accordance with this preferred alternate exemplary embodiment of the present invention, a linear optical scanning mechanism 210 is provided and is selectively located preferably directly above the slots within which a solid pharmaceutical product blister package card is provided. This embodiment is compatible with the storage drawers of the embodiments described above, for example.

Although the location of the optical scanning mechanism with respect to the storage slots has not been shown, those skilled in the art will appreciate that it is preferably located such that the device is centered over the solid pharmaceutical product blister package card storage slot. Additionally, with respect to the access control device described below, it should be recognized that this scanner could readily be secured within the aperture of the mechanism. Alternatively, the reader could be located separately from the drawer member altogether.

As shown in the illustration, the linear optical scanning mechanism is shown at 210, wherein the transmitting and receiving portions of the scanner 211 and 212 are respectively provided on opposite sides of a blister package member 214. The linear optical scanning mechanism is used to determine which individual blister cavities within the overall blister package member 214 have been utilized. This is an alternative to the use of the electrical card reading mechanism described above wherein the edge connector is interfaced with electrical conductors that are used to read information from the conductive members on the sides of the blister card.

Those skilled in the art will appreciate that the card reader mechanism described with reference to FIG. 27 can employ a variety of different types of optical reading mechanisms. For example, imaging elements such as CCD arrays and CMOS sensors may be interchangeably used in order to provide the requisite imaging data to determine whether a particular blister package cavity has been emptied. In an alternate embodiment, simple optical transceivers may be used which are located in registry with the columns of blister package cavities so that the contents of the overall package can be easily automatically determined. In such an embodiment, it may also be preferable to include registration marks along one or more sides of the blister package in order to effect triggering of the reading mechanism at the appropriate time so that reading is initiated for each cavity when the center is located across from a blister package cavity.

Figure 28:
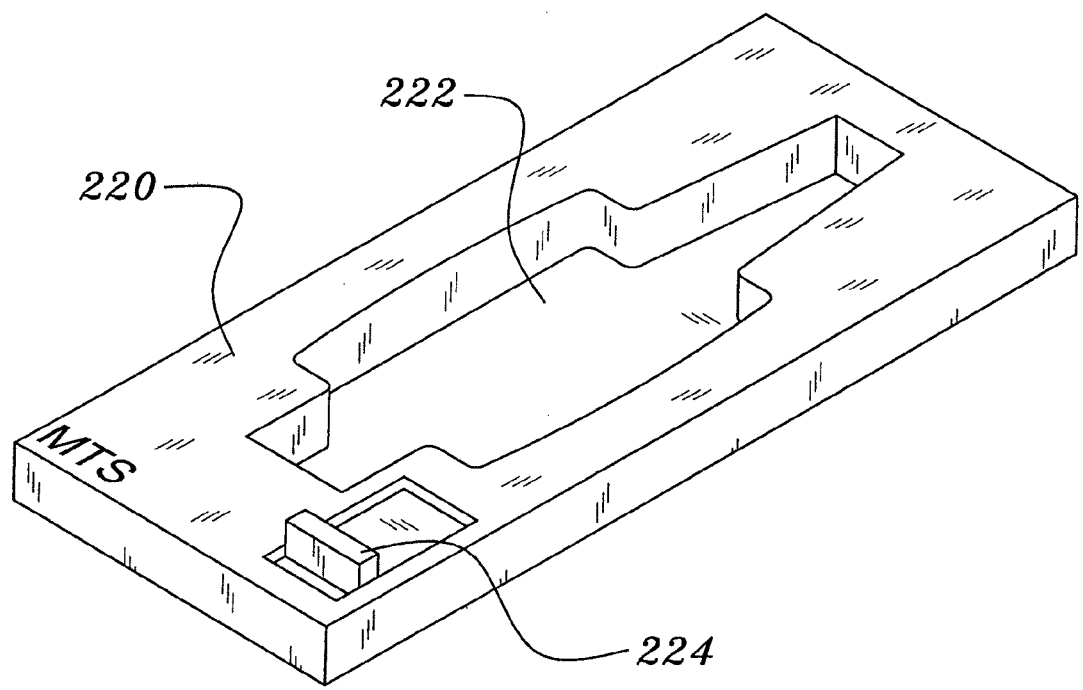
FIG. 28 illustrates an alternate preferred exemplary embodiment of the present invention.

FIG. 28 illustrates yet another alternate preferred exemplary embodiment of the present invention wherein a card removal and insertion aperture mechanism is provided to limit access to the individual blister package card member which is shown generally at 220.

As illustrated in FIG. 28, the card removal and insertion aperture mechanism 220 is preferably moveably secured over the drawer within which individual blister package cards are located. Although the drawer and/or the slots of the drawer have not been shown in this illustration for the sake of convenience, those skilled in the art will appreciate that the aperture mechanism 220 may be either fixed or movably positioned over individual slots of the drawer Operation of this device is described in more detail below.

The card removal and insertion aperture 220 preferably includes a slotted opening 222 that is sufficiently large to allow users to insert and remove blister package cards and/or frames containing blister cards from a slot in the drawer over which the aperture mechanism 220 is located.

Advantageously, the insertion and removal aperture can be used to limit access to the blister package cards contained within the drawer. Additionally, the card insertion and removal aperture preferably includes a slide mechanism 224 that may be used to engage/disengage an electrical connection to the card. This is described in more detail below. As noted above, the aperture mechanism 220 may also incorporate the optical scanning or reading mechanisms described above including text reading mechanisms so that information that is printed or otherwise located on the blister package can be read during insertion or removal of the blister package card.

FIG. 29 illustrates yet another alternate preferred embodiment of the present invention wherein an angled surface is preferably provided on a side of the blister card member. This embodiment is shown generally at 230 in FIG. 29A.

In this preferred alternate exemplary embodiment, the edge of the blister card is preferably designed at a gradual angle of preferably approximately 5° and a connector member 230 is engineered on this side to interface with a corresponding angle feature of a receiving connector 235 within the storage device. It should be recognized that the angle portion of the card is not necessary and specifically that this embodiment will work with a blister package card having perpendicular side edges. The connector member 230 is secured against the side of an opposite angled receiving connector 235 within the drawer.

Metal contacts on the card similar to those described above for determining contents of the blister package card cavities interface with the corresponding contacts within the connector member 230. The illustration of FIG. 29A shows the blister package card 239 during insertion. Spring finger metal contacts 237 on the connector member 230 mate with corresponding electrical contacts 238 are used in order to electrically communicate with the card and identify which individual cavities within the overall package have been utilized. FIG. 29B illustrates the blister package card after insertion within the drawer.

Figure 30A:
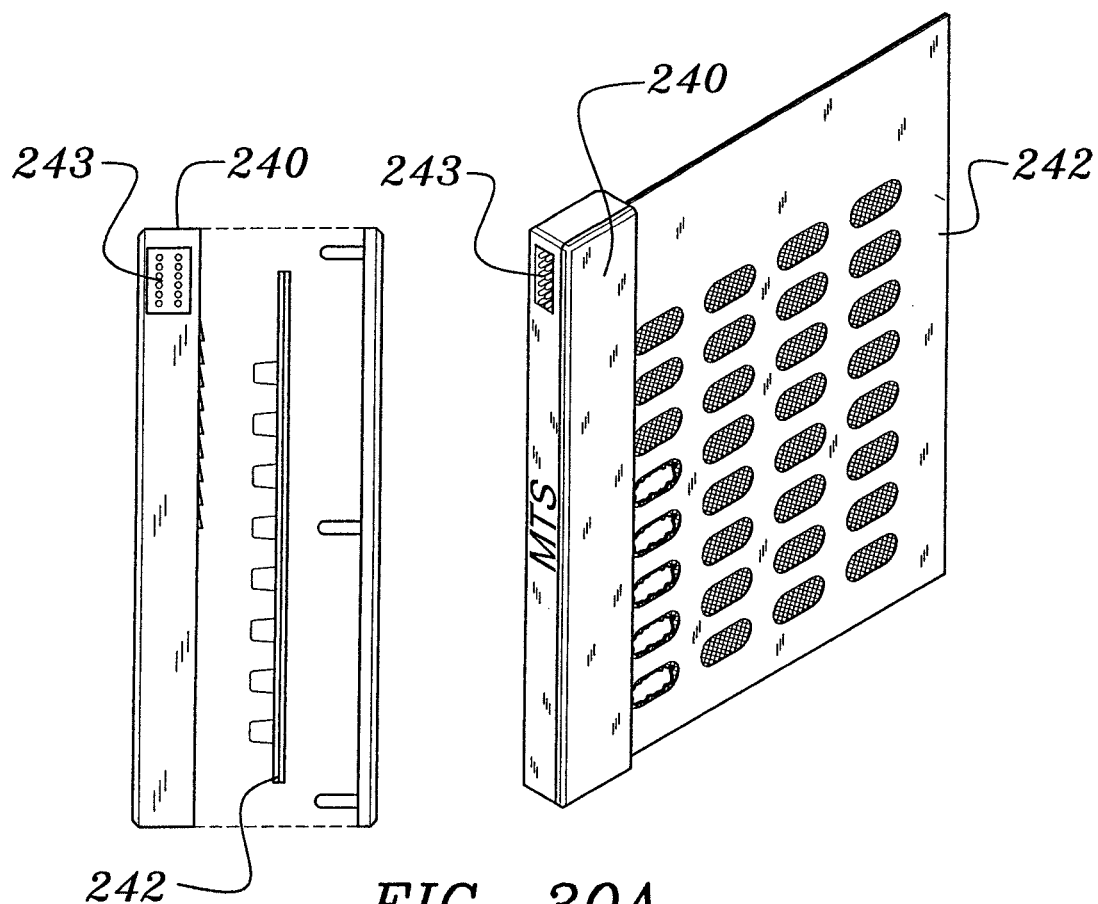
FIG. 30 illustrates an alternate preferred exemplary embodiment of the present invention.
Figures 30B, 30C:
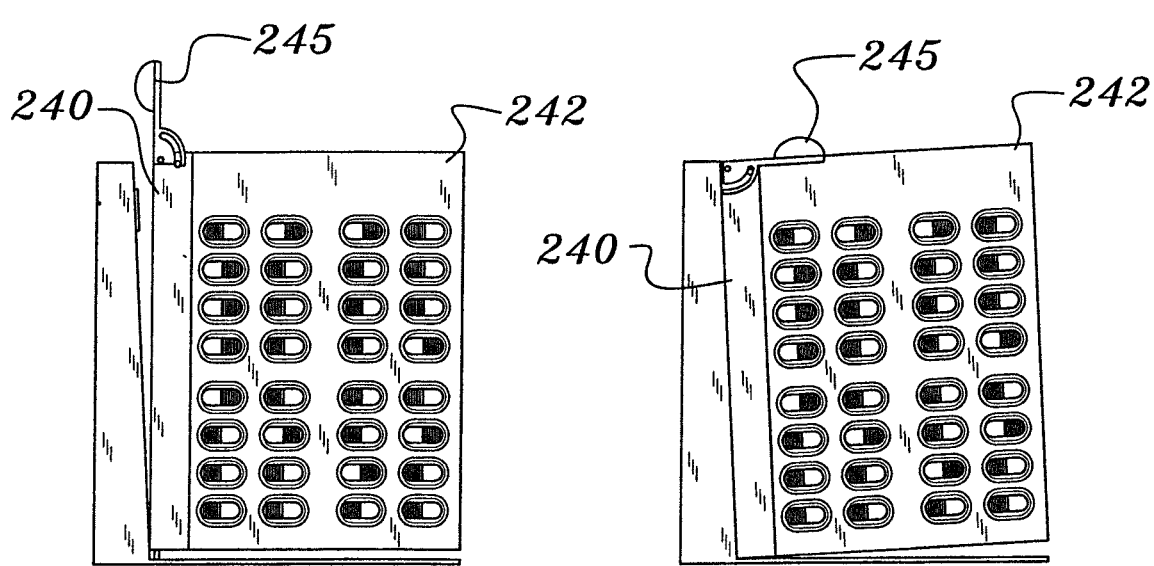

FIG. 30A-C illustrate yet another alternate embodiment of the present invention, wherein the blister package card is secured into an electrical interface mechanism which may have various different configurations. Regardless of the specific configuration, electrical contacts that are formed on the card member for determining the locations of the used medications interface with the interface mechanism 240 that is secured to the contact members on the blister package card member 242.

FIG. 30A illustrates an electrical interface mechanism 240 that is secured to the blister package card member 242 in order to provide secure electrical communication with the blister package card. In the preferred exemplary embodiment, the electrical interface mechanism 240 preferably includes an electrical connector 243 which mates with a corresponding electrical connector of the storage mechanism so that the appropriate electrical signals may be transmitted to the blister package card member 242.

FIG. 30B is an alternate embodiment wherein the electrical interface mechanism 240 also preferably includes a lever 245 that is used to press opposite sides of the electrical interface mechanism 240 toward each other with the electrical contacts of the blister package card member 242 therebetween. This compressive action is useful in ensuring that appropriate electrical connection is made with the electrical contacts of the blister package 242. The cam action of a lever 245 forces together portions of the electrical interface mechanism 240 on opposite sides of the blister card 242 thereby ensuring an improved electrical connection.

FIG. 30C illustrates the lever in the closed position.

Figures 31A, 31B:
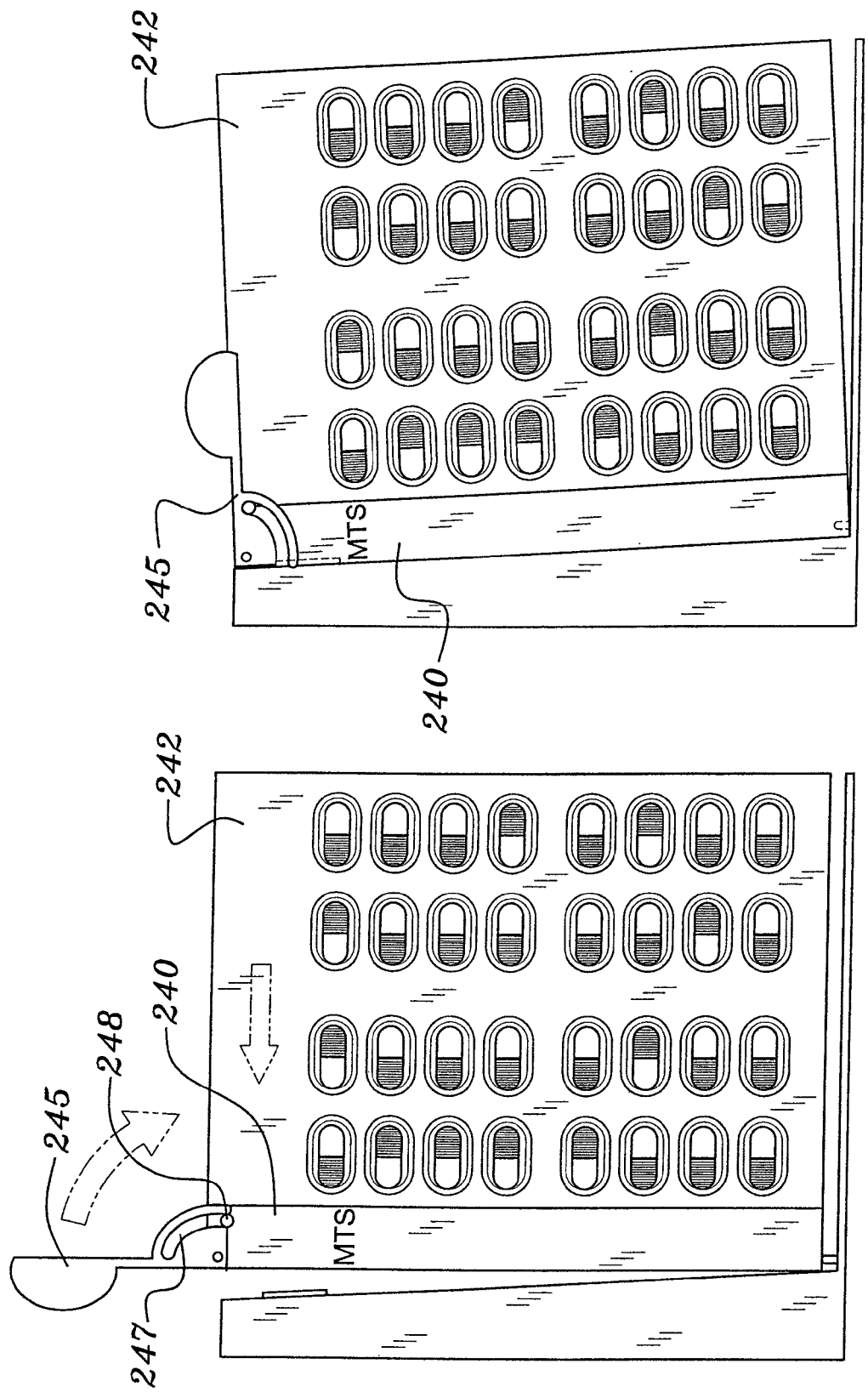
FIG. 31 illustrates an alternate preferred exemplary embodiment of the present invention.

FIG. 31 illustrates the operation of the lever mechanism to secure the blister card and also ensure that there is proper electrical connection. FIG. 31A illustrates the cam action lever 245 in the disengaged position wherein the blister package card member 242 may be easily removed. A slot 247 located in each side of the lever 245 engages a corresponding pin 248 that is also located on each side of the electrical interface mechanism 240. The space between the slotted portions of the lever 245 decreases such that rotation of the lever in a clockwise direction forces the two opposite sides of the electrical interface mechanism 240 toward each other thereby securing the blister card package member 242 therein and ensuring appropriate electrical contact between the contacts of the blister package card 242 and they electrical interface mechanism 240. Advantageously, when the lever 245 is moved to the open position, it disengages the electrical interface mechanism 240 and the lever mechanism 245 may also be used as a handle for easy removal of the blister package card 242 from the slot.

FIG. 32 illustrates an alternate preferred exemplary embodiment of the present invention which is generally shown at 250. In accordance with this alternate preferred exemplary embodiment, a solenoid injector/ejector is provided in order to aid in the selective removal of blister card package members from a storage device.

In accordance with this preferred exemplary embodiment, a mechanical bar 252 is provided perpendicular to a row of cards. An angled member 253 protrudes from the bar at an angle to the axis of the bar and the angled feature engages the corresponding blister package card in order to prevent removal of the blister package card from the slot of the drawer within which the blister package cards are located. This is illustrated in FIG. 32A wherein the angled members 253 are each position over the blister package card members. FIG. 32 B illustrates the axial displacement of the bar member 252.

When the bar 252 is translated axially, the bar member 252 moves such that it engages and disengages the blister package card members 254. The system disengages the cards upon initial interface with the system by the user and reengages all cards when the user is complete. FIG. 32C illustrates the axial displacement of the bar member 252 such that access to all of the blister package card members to 254 is provided.

Figure 33:
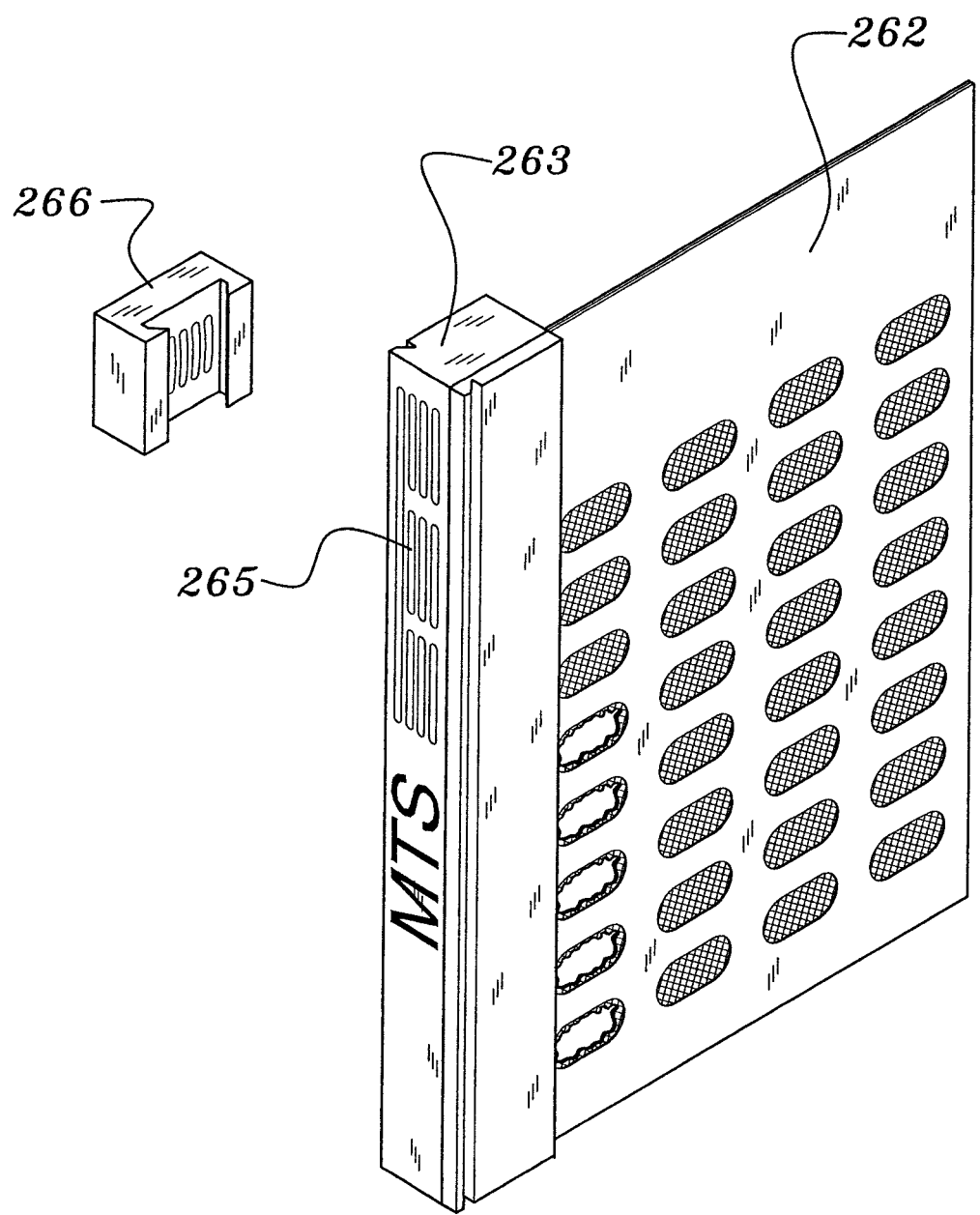
FIG. 33 illustrates an alternate preferred exemplary embodiment of the present invention.

FIG. 33 illustrates a slide reader mechanism wherein a blister package card 262 is inserted into an electrical interface member 263. The electrical interface member 263 has a plurality of contacts 265 which can be read by a slide reading mechanism 266.

Figure 34:
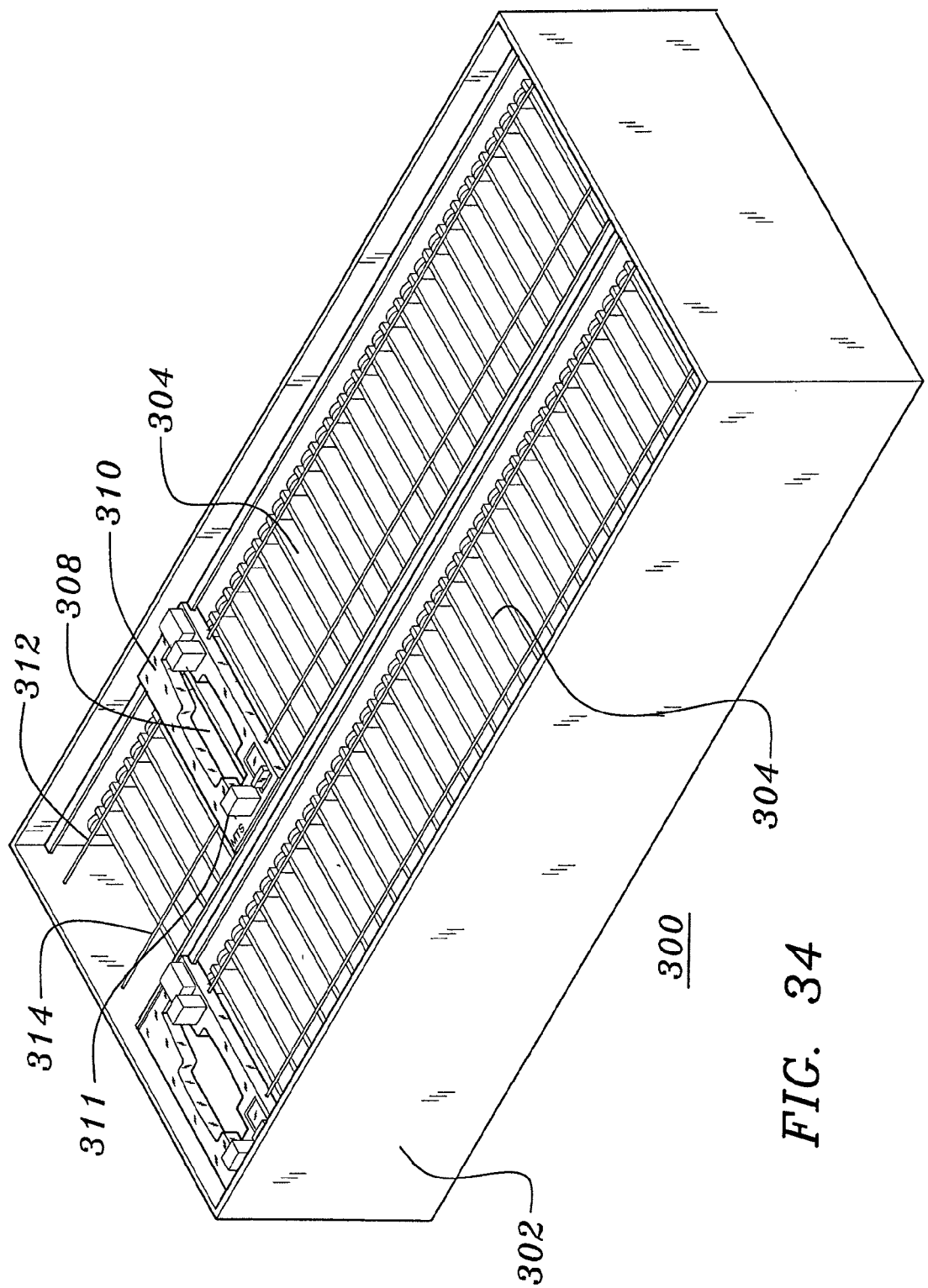
FIG. 34 illustrates an alternate preferred exemplary embodiment of the present invention.

FIG. 34 illustrates a storage mechanism for use in accordance with the presently preferred embodiments of the present invention, wherein selective access to the blister package card members and/or frames holding the card members is provided by an opening in an access guard. This alternate preferred exemplary embodiment of the present invention is shown generally at 300 wherein a drawer 302 includes a plurality of blister package card members 304 arranged in two adjacent rows on opposite sides of the drawer 302.

The access guard 310 or aperture member traverses across the top of at least one side of the storage drawer 302. Advantageously, in accordance with the preferred embodiment of the present invention, access restricting mechanisms 312, 314 are provided to eliminate the possibility of the removal of any of the blister package members that are not located at the opening of the access mechanism 310.

The access guard member or aperture member 310 may be embodied as the aperture mechanism described above and preferably includes an opening 308 which is sufficiently large to enable a user to readily remove one of the blister package card members 304 while restricting access to adjacent blister card package members. Advantageously, the access restricting mechanisms 312, 314 are preferably secured to the access guard member 310 such that they traverse across the tops of the blister card package members 304 with the access guard member 310. Advantageously these access restricting mechanisms 312, 314 prevent individuals from removing any of the blister package card members that are not physically located at the position of the access guard member 310.

FIG. 34 also illustrates the bar code reader 311 or rendering mechanism described above for reading information from the package for automatically identifying the contents thereof.

The access restricting mechanisms 312, 314 may be embodied as wire cables, durable plastic tape, or a linkage of individual members such that they restricting mechanisms 312, 314 may be readily traversed along with the access guard member 310. Those skilled in the art will appreciate that the access restricting mechanisms may be continuous members that wrap around beneath the drawer and are transmitted across pulleys in order to ensure the easy movement of the overall device.

In a preferred exemplary embodiment of the present invention, the system is motor driven and automatically traverses the access guard member 310 to the appropriate slot within which a desired medication is located based on the computer control of the system as described above. In an alternate arrangement lights are used as with the embodiments described above to enable users to easily identify the appropriate slot for manually sliding and locating the access guard member 310.

In accordance with a preferred exemplary embodiment of the present invention, the access restricting mechanism 310 preferably includes a solenoid driven latching mechanism which further restricts access to the blister cards and ensures that only the appropriately designated card within a slot is removed by a user. For example, based on position information that is fed back to the computer controller, the system will only disengage the locking latch of the position restricting mechanism 310 when the position restricting mechanism is appropriately located by user. This alternate embodiment will prevent access to the blister cards during the traverse of the access restricting mechanism 310. Specifically, in this alternate arrangement, the opening 308 includes a solenoid driven latching mechanism that crosses the opening 308 with a stiff structure such that it prevents removal of a blister package card and/or frame containing a card within the drawer until such time as the system authorizes the removal of the card. Those skilled in the art will also appreciate that virtually any locking mechanism may be employed for this purpose. However, it is preferred that it is electromechanically operated for automatic operation.

In an alternate embodiment, the system employs a small door over the opening that is electronically locked/unlocked for the purpose of restricting access.

Figure 35:
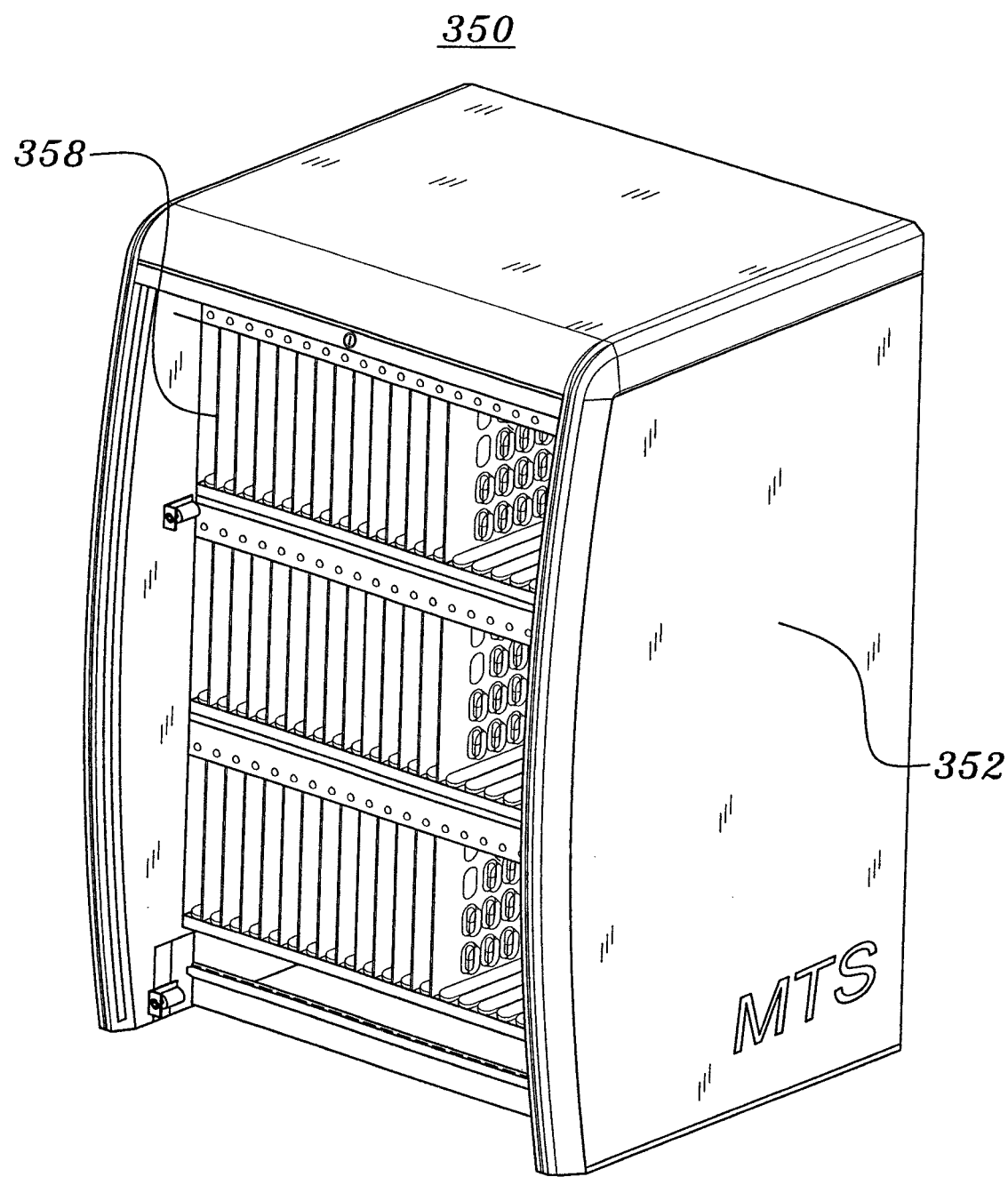
FIG. 35 illustrates an alternate preferred exemplary embodiment of the present invention.

FIG. 35 illustrates an alternate preferred exemplary of the embodiment of the present invention which is shown generally at 350 in accordance with this preferred alternate exemplary embodiment a storage mechanism 352 includes a plurality of solid pharmaceutical blister package card members 358 that are preferably arranged in a plurality of rows of card members.

In accordance with this preferred alternate exemplary embodiment a rolling door that is not shown is provided and this door may be selectively positioned over each of the respective rows of blister package card members. Depending upon access that is provided to a user, the rolling door may be limited in its movement to only provide access to the first row of blister package card members. Additional levels of access may be provided to any remaining rows. In the illustration of FIG. 35, the roll top drawer is shown in its retracted position wherein all rows are accessible. The sliding drawer preferably operated in similar fashion to a roll top desk. However, in the preferred embodiment the door member is comprised of durable plastic linear members that linked along sides thereof. Access to the different rows is restricted through solenoid driven pins which are located to stop the door as desired.

Accordingly, through this mechanism, multiple levels of access may be provided. For example, a first level of access may provide all users with access to a first one of the rows of blister package card members. The locking mechanism may selectively permit certain users or individuals at certain times to selectively access the second row and/or the third row. Accordingly, the system is thus able to provide multiple levels of restricted access.

We claim:

1. An automated medication dispensing system, comprising,
    a medical information system; and
    a storage/dispenser unit, where said storage/dispenser unit comprises a processor and a compartment, and further wherein the medical information system is accessible via a mobile computer system terminal device and the storage/dispenser unit is located in a mobile unit that is in communication with the medical information system, the storage/dispenser unit automatically providing a user with identification of a medication location for a particular patient based on information that is received from the medical information system, and further comprising a plurality of individually removable frame structures that provide electrical communication with a corresponding plurality of solid pharmaceutical product packages, and further wherein each frame structure has a corresponding product package secured in the frame structure and each product package includes a plurality of individual solid pharmaceutical cavity locations, each of the individual cavity locations having corresponding wirings that provide information regarding whether a specific one of the plurality of solid pharmaceutical cavity locations has been accessed and wherein each of the plurality of frame structures is removable from the storage/dispenser unit such that each frame structure may be separately transported to a patient location that is different from a location of the storage/dispenser unit and each frame structure transfers electrical signals specifically identifying whether one or more of the plurality of solid pharmaceutical cavity locations of the product package secured in the frame structure has been accessed to the mobile computer system terminal device.

2. An automated medication dispensing system as in claim 1, where said medical information system is a computer.

3. An automated medication dispensing system as in claim 1, where said storage/dispenser unit further comprises an opening mechanism to automatically open said compartment.

4. An automated medication dispensing system as in claim 3, where said compartment further comprises a medication package receiver.

5. An automated medication dispensing system as in claim 4, where said compartment further comprises an information reader.

6. An automated medication dispensing system as in claim 5, where said medical information system is attached to said storage/dispenser unit.

7. An automated medication dispensing system as in claim 6, where said storage/dispenser unit comprises multiple individual product packages.

8. An automated medication dispensing system as in claim 7, where each product package includes a medication package indicator.

9. An automated medication dispensing system, comprising in combination,
    a means for retrieving prescription medication information; and
    a means for storing medication, where said means for storing medication comprises a means for processing information, with means for storing individual medication packages and a means for determining the content of said means for storing medication, and further wherein the means for retrieving prescription medication information is a medical information system that is accessible via a mobile computer system terminal device and the means for storing medication is a storage/dispenser unit that is located in a mobile unit that is in communication with the medical information system, the storage/dispenser unit automatically providing a user with identification of a medication location for a particular patient based on information that is received from the medical information system and further comprising a plurality of individually removable frame structures that provide electrical communication with a corresponding plurality of solid pharmaceutical product packages, and further wherein each frame structure has a corresponding product package secured in the frame structure and each product package includes a plurality of individual solid pharmaceutical cavity locations, each of the individual cavity locations having corresponding wirings that provide information regarding whether a specific one of the plurality of solid pharmaceutical cavity locations has been accessed and wherein each of the plurality of frame structures is removable from the storage/dispenser unit such that each frame structure may be separately transported to a patient location that is different from a location of the storage/dispenser unit and each frame structure transfers electrical signals specifically identifying whether one or more of the plurality of solid pharmaceutical cavity locations of the product package secured in the frame structure has been accessed to the mobile computer system terminal device.

10. An automated medication dispensing system as in claim 9, where said means for storing medication further comprises a means for automatically opening said means for storing individual medication packages.

11. An automated medication dispensing system as in claim 10, where said means for storing individual medication packages further comprises a means for reading information about medication from the medication package.

12. A method of storing and dispensing medication comprising the steps of:
retrieving medication information from a medical information system;
communicating said medication information to a storage/dispenser unit with a processor and a compartment, where said processor retrieves information about the content of said compartment; and
said storage/dispenser unit automatically dispenses the medication in response to the medication information, and further wherein the medical information system is accessible via a mobile computer system terminal device and the storage/dispenser unit is located in a mobile unit that is in communication with the medical information system, the storage/dispenser unit automatically providing a user with identification of a medication location for a particular patient based on information that is received from the medical information system and further comprising a plurality of individually removable frame structures that provide electrical communication with a corresponding plurality of solid pharmaceutical product packages, and further wherein each frame structure has a corresponding product package secured in the frame structure and each product package includes a plurality of individual solid pharmaceutical cavity locations, each of the individual cavity locations having corresponding wirings that provide information regarding whether a specific one of the plurality of solid pharmaceutical cavity locations has been accessed and wherein each of the plurality of frame structures is removable from the storage/dispenser unit such that each frame structure may be separately transported to a patient location that is different from a location of the storage/dispenser unit and each frame structure transfers electrical signals specifically identifying whether one or more of the plurality of solid pharmaceutical cavity locations of the product package secured in the frame structure has been accessed to the mobile computer system terminal device.

13. A method of storing and dispensing medication as in claim 12, further comprising the step of indicating a specific medication package within said compartment.

* * * * *